US008193314B2

(12) United States Patent
Stephanopoulos et al.

(10) Patent No.: US 8,193,314 B2
(45) Date of Patent: Jun. 5, 2012

(54) TRANSCRIPTIONAL ENGINEERING OF LACTOBACILLUS

(75) Inventors: Gregory Stephanopoulos, Winchester, MA (US); Daniel Klein-Marcuschamer, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 319 days.

(21) Appl. No.: 12/170,617

(22) Filed: Jul. 10, 2008

(65) Prior Publication Data

US 2009/0176659 A1 Jul. 9, 2009

Related U.S. Application Data

(60) Provisional application No. 60/959,317, filed on Jul. 12, 2007.

(51) Int. Cl.
C07K 14/00 (2006.01)
(52) U.S. Cl. ........................................................ 530/350
(58) Field of Classification Search .................. 530/350
See application file for complete search history.

(56) References Cited

U.S. PATENT DOCUMENTS 6,518,065 B1  2/2003  Stemmer
2007/0072194 A1*  3/2007  Alper et al. ........................ 435/6

FOREIGN PATENT DOCUMENTS

WO  WO 2007/038564 A2  4/2007

OTHER PUBLICATIONS

Alper, H., Development of systematic and combinatorial approaches for the metabolic engineering of microorganisms. Thesis at Massachusetts Institute of Technology submitted Apr. 3, 2006. pp. 3-261.
Alper et al., Engineering yeast transcription machinery for improved ethanol tolerance and production. Science. Dec. 8, 2006; 314(5805):1565-8.
Alper et al., Global transcription machinery engineering: a new approach for improving cellular phenotype. Metab Eng. May. 2007;9(3):258-67. Epub Jan 8, 2007.
Aukrust et al., Transformation of Lactobacillus by electroporation. Methods Mol Biol. 1995;47:201-8.
Azcarate-Peril et al., Identification and inactivation of genetic loci involved with Lactobacillus acidophilus acid tolerance. Appl Environ Microbiol. Sep. 2004;70(9):5315-22.
Beltran et al., Interrogating genomes with combinatorial artificial transcription factor libraries: asking zinc finger questions. Assay Drug Dev Technol. Jun 2006;4(3):317-31. Review.
Booth, I.R., Regulation of cytoplasmic pH in bacteria. Microbiol Rev. Dec 1985;49(4):359-78. Review.
Campbell et al., Structure of the bacterial RNA polymerase promoter specificity sigma subunit. Mol Cell. Mar. 2002;9(3):527-39.

Day et al., Post-transcriptional gene regulatory mechanisms in eukaryotes: an overview. J Endocrinol. Jun. 1998;157(3):361-71. Review.
Dombroski et al., Polypeptides containing highly conserved regions of transcription initiation factor sigma 70 exhibit specificity of binding to promoter DNA. Cell. Aug. 7, 1992;70(3):501-12.
Duy et al., The proteome and transcriptome analysis of Bacillus subtilis in response to salicylic acid. Proteomics. Mar. 2007;7(5):698-710.
Elowitz, et al., Stochastic gene expression in a single cell. Science. Aug. 16, 2002;297(5584):1183-6.
Errington, J., Possible intermediate steps in the evolution of a prokaryotic developmental system. Proc Biol Sci. May 22, 1991;244(1310):117-21. Review.
Franck et al., Measurement of intracellular pH in cultured cells by flow cytometry with BCECF-AM. J Biotechnol. May 15, 1996;46(3):187-95.
Giraud et al., Influence of pH and initial lactate concentration on the growth of Lactobacillus-plantarum. Appl Microbiol Biotechnol. 1991;36:96-99.
Hansen et al., Visual clone identification of Penicillium commune isolates. J Microbiol Methods.Feb. 2003;52(2):221-9.
Ideker et al., Discovering regulatory and signalling circuits in molecular interaction networks. Bioinformatics. 2002;18 Suppl 1:S233-40.
Imashimizu et al., The cyanobacterial principal sigma factor region 1.1 is involved in DNA-binding in the free form and in transcription activity as holoenzyme. FEBS Lett. Jun. 2, 2006;580(14):3439-44. Epub May 12, 2006.
Kelley et al., Conserved pathways within bacteria and yeast as revealed by global protein network alignment. Proc Natl Acad Sci U S A. Sep. 30, 2003;100(20):11394-9. Epub 2003 Sep 22.
Kleerebezem et al., Complete genome sequence of Lactobacillus plantarum WCFS1. Proc Natl Acad Sci U S A. Feb. 18, 2003;100(4):1990-5. Epub Feb. 3, 2003.
Klein-Marcuschamer et al., Assessing the potential of mutational strategies to elicit new phenotypes in industrial strains. Proc Natl Acad Sci U S A. Feb. 19, 2008;105(7):2319-24. Epub Feb. 5, 2008.
Kok et al., Construction of plasmid cloning vectors for Lactic Streptococci which also replicate in Bacillus subtilis and Escherichia coli. Appl Environ Microbiol. Oct. 1984;48(4):726-31.
Kresnowati et al., Measurement of fast dynamic intracellular pH in Saccharomyces cerevisiae using benzoic acid pulse. Biotechnol Bioeng. May 1, 2007;97(1):86-98.
Liao et al., Network component analysis: reconstruction of regulatory signals in biological systems. Proc Natl Acad Sci U S A. Dec. 23, 2003;100(26):15522-7. Epub Dec. 12, 2003.
McDonald et al., Acid Tolerance of Leuconostoc mesenteroides and Lactobacillus plantarum. Appl Environ Microbiol. Jul. 1990;56(7):2120-2124.
Murphy et al., Oxygen dependent lactate utilization by Lactobacillus plantarum. Arch Microbiol. Feb. 1985;141(1):75-9.

(Continued)

Primary Examiner — Karen Carlson
(74) Attorney, Agent, or Firm — Wolf, Greenfield & Sacks, P.C.

(57) ABSTRACT

The invention relates to global transcription machinery engineering to produce altered cells having improved phenotypes and methods for evaluating phenotypic diversity.

5 Claims, 8 Drawing Sheets

OTHER PUBLICATIONS

Park et al., Identification and use of zinc finger transcription factors that increase production of recombinant proteins in yeast and mammalian cells. Biotechnol Prog. May-Jun. 2005;21(3):664-70.

Park et al., Phenotypic alteration and target gene identification using combinatorial libraries of zinc finger proteins in prokaryotic cells. J Bacteriol. Aug. 2005;187(15):5496-9.

Park et al., Phenotypic alteration of eukaryotic cells using randomized libraries of artificial transcription factors. Nat Biotechnol. Oct. 2003;21(10):1208-14. Epub Sep. 7, 2003. Erratum in: Nat Biotechnol. Apr. 2004;22(4):459.

Patnaik et al., Genome shuffling of *Lactobacillus* for improved acid tolerance. Nat Biotechnol. Jul. 2002;20(7):707-12.

Pieterse et al., Unravelling the multiple effects of lactic acid stress on *Lactobacillus plantarum* by transcription profiling. Microbiology. Dec. 2005;151(Pt12):3881-94.

Porro et al., Replacement of a metabolic pathway for large-scale production of lactic acid from engineered yeasts. Appl Environ Microbiol. Sep. 1999;65(9):4211-5.

Posno et al., Incompatibility of *Lactobacillus* Vectors with Replicons Derived from Small Cryptic *Lactobacillus* Plasmids and Segregational Instability of the Introduced Vectors. Appl Environ Microbio. Jun. 1991; 57(6):1822-1828.

Spilimbergo et al., Determination of extracellular and intracellular pH of *Bacillus subtilis* suspension under CO2 treatment. Biotechnol Bioeng. Nov. 20, 2005;92(4):447-51.

Stephanopoulos, et al., Exploiting biological complexity for strain improvement through systems biology. Nat Biotechnol. Oct. 2004;22(10):1261-7.

Stephanopoulos, G., Metabolic engineering by genome shuffling. Nat Biotechnol. Jul. 2002;20(7):666-8.

Swain et al., Intrinsic and extrinsic contributions to stochasticity in gene expression. Proc Natl Acad Sci U S A. Oct. 1, 2002;99(20):12795-800. Epub Sep. 17, 2002.

Tian et al., Accurate multiplex gene synthesis from programmable DNA microchips. Nature. Dec.23, 2004;432(7020):1050-4.

Yang et al., Inferring yeast cell cycle regulators and interactions using transcription factor activities. BMC Genomics. Jun. 10, 2005;6(1):90.

Yeang et al., Validation and refinement of gene-regulatory pathways on a network of physical interactions. Genome Biol. 2005;6(7):R62. Epub Jul. 1, 2005.

Zhang et al., Genome shuffling leads to rapid phenotypic improvement in bacteria. Nature. Feb. 7, 2002;415(6872):644-6.

Gansel, X. et al., "Partial Characterization of an *rpoD*-Like Gene of *Lactoccocus lactis* subsp. *lactis* ML3 with a Polymerase Chain Reaction-Based Approach," *Current Microbiology* 1993;27:267-271.

Paget, M.S.B. et al., "The $\sigma^{70}$ family of sigma factors," *Genome Biology* 2003; 4:203.

* cited by examiner

U.S. 8,193,314 B2

TRANSCRIPTIONAL ENGINEERING OF LACTOBACILLUS

RELATED APPLICATIONS

This application claims priority under 35 U.S.C. §119(e) to U.S. provisional application 60/959,317, filed Jul. 12, 2007, the disclosure of which is incorporated herein by reference.

GOVERNMENT INTEREST

This work was funded in part by the National Science Foundation under grant number 6895619. The government has certain rights in this invention.

FIELD OF THE INVENTION

The invention relates to global transcription machinery engineering to produce altered cells having improved phenotypes and methods for evaluating phenotypic diversity.

BACKGROUND OF THE INVENTION

Developing improved strains for industrial bioconversions can be achieved through different approaches. When the pathways or networks of interest are simple and have been characterized, the responsible genes can be manipulated accordingly. On the other hand, when a trait of interest is poorly understood and when high throughput screening methods are available, random approaches can be used (30). This is especially useful for complex phenotypes that result from simultaneous action of several genes and for which detailed mechanistic information may be lacking. Stresses encountered in industrial fermentations, such as high temperature, acidity, and osmotic pressure, commonly elicit this type of complex responses (29). Therefore, obtaining robust biocatalysts has been traditionally done through serial rounds of mutagenesis and selection. More recently, gene shuffling has improved on asexual breeding through multi-parental mating of whole cells (25, 32). One limitation of these approaches is that they create untransferable and intractable changes at the genomic level.

Even when the loci involved in a complex response are known, it is unclear what modifications to implement for improving it, as the phenotypic response is connected to the genotype indirectly through the transcriptome and proteome (10). Many efforts in whole-cell engineering have recognized the more direct mapping between transcriptome and phenotype and have tried to manipulate the transcript profile directly (1, 2, 5, 22-24). Global transcription machinery engineering (gTME) has been used successfully to introduce multilocus responses at the transcriptomic level that are transferable between strains. Random mutagenesis of the TATA-binding protein of *Saccharomyces cerevisiae* has resulted in mutants with increased ethanol tolerance and productivity (1). By applying the same concept to the principal sigma factor of *Escherichia coli* strains with improved resistance to ethanol and SDS, and with increased lycopene accumulation have been produced (2).

SUMMARY OF THE INVENTION

In the present study, we engineered the principal sigma factor of *Lactobacillus plantarum* for improving its tolerance to high lactic acid and low pH conditions.

The invention utilizes global transcription machinery engineering to produce altered cells having improved phenotypes. In particular, the invention is demonstrated through the generation of mutated bacterial sigma factors with varying preferences for promoters on a genome-wide level. The cells resulting from introduction of the mutated sigma factors have rapid and marked improvements in phenotypes, such as tolerance of deleterious culture conditions or improved production of metabolites.

The introduction of mutant transcription machinery into a cell, combined with methods and concepts of directed evolution, allows one to explore a vastly expanded search space in a high throughput manner by evaluating multiple, simultaneous gene alterations in order to improve complex cellular phenotypes.

According to several aspects of the invention, mutant sigma factors are provided, preferably *Lactobacillus* sigma factors, and more preferably rpoD. The mutant sigma factors include mutation of glutamine 345, preferably to lysine; one or more of mutations of A44, K74, A114, and A119, preferably A44T, K74R, A114D, and A119S; one or more mutations in the region that binds the −10 promoter box (amino acids M155-Q228); or one or more mutations in the region that binds the −35 promoter box (amino acids G276-E368). Other sigma factors of *Lactobacillus* or sigma factors of other bacterial strains also can be mutated in equivalent amino acids or regions to provide other mutant sigma factors.

In some embodiments, the sigma factor, preferably rpoD, is truncated. In a particular embodiment, rpoD sigma factor comprises 119 amino terminal amino acids of the wild type protein.

In some embodiments, the mutant *Lactobacillus* rpoD sigma factor includes a nonsynonymous substitution at amino acid Q345, or equivalent amino acid in other sigma factors of *Lactobacillus* or of other bacterial strains. In certain embodiments, the nonsynonymous substitution is a lysine.

In some embodiments, the sigma factor is rpoD, rpoF, rpoS, rpoH, rpoN, rpoE, fecI and sigH; preferably the sigma factor is rpoD.

In any of the embodiments, the other bacterial strain is an *E. coli* strain.

Also provided according to the invention are isolated nucleic acid molecules encoding the mutant sigma factors, vectors comprising such isolated nucleic acid molecules, and bacterial cells or strains including the mutant sigma factors, the isolated nucleic acid molecules, or the vectors. In certain embodiments, the cell or strain is a *Lactobacillus* cell or strain. More preferably, the cell or strain is optimized for the production of lactate prior to introducing into the bacterial cell or strain the mutant *Lactobacillus* rpoD sigma factor, the isolated nucleic acid molecule, or the vector.

According to another aspect of the invention, methods for producing lactate, a lactate metabolite or a lactate intermediate are provided. The methods include culturing the foregoing bacterial cells or strains. In some embodiments, the methods also include recovering the lactate, the lactate metabolite or the lactate intermediate from the bacterial cells, strains or the culture thereof. In certain embodiment, the cells are cultured in a low pH culture medium. In some embodiments, the low pH of the culture medium is obtained by acidifying the culture medium with an acid. Exemplary acids include lactic acid or hydrochloric acid.

In another aspect of the invention, methods for producing a *Lactobacillus* cell having altered production of lactate are provided. The methods include mutating global transcription machinery of a *Lactobacillus* cell that produces lactate to produce an altered cell, and isolating altered cells that produce increased or decreased amounts of lactate. Preferably the *Lactobacillus* cell is *L. plantarum*. In some embodiments, the *Lactobacillus* cell is optimized for production of lactate prior to mutating the global transcription machinery.

In other embodiments, the global transcription machinery is a sigma factor of the *Lactobacillus* cell. Preferably the sigma factor is encoded by rpoD. Optionally the sigma factor is encoded by in an expression vector.

In further embodiments, the global transcription machinery is mutated by directed evolution. In preferred embodiments, the directed evolution is performed using error prone PCR or gene shuffling.

In still other embodiments, the mutation(s) in the global transcription machinery is/are one or more point mutations and/or one or more truncations or deletions. In some embodiments, the truncation does not include the promoter binding region of the global transcription machinery.

Also provided by the invention are collections of cells produced by the foregoing methods. The invention also provides methods of producing lactate, a lactate metabolite or a lactate intermediate, that include culturing the cells produced by the foregoing methods. In some embodiments, the methods also include recovering the lactate, the lactate metabolite or the lactate intermediate from the cells or the cell cultures. In certain embodiment, the cells are cultured in a low pH culture medium. In some embodiments, the low pH of the culture medium is obtained by acidifying the culture medium with an acid. Exemplary acids include lactic acid or hydrochloric acid.

According to another aspect of the invention, methods for improving a phenotype of a cell are provided. The methods include mutating global transcription machinery of a *Lactobacillus*, introducing the mutated *Lactobacillus* global transcription machinery into the cell, and selecting altered cells for a predetermined phenotype. In some embodiments, the methods further include isolating altered cells that have an improved phenotype. In certain embodiments, the step of selecting includes culturing the altered cell under selective conditions and/or high-throughput assays of individual cells for the phenotype. In some embodiments, the cell is optimized for the phenotype prior to introducing the mutated *Lactobacillus* global transcription machinery into the cell. In certain embodiments, the global transcription machinery is a sigma factor of the *Lactobacillus* cell, optionally one encoded by rpoD and/or encoded by an expression vector.

In some embodiments, the global transcription machinery is mutated by directed evolution, optionally performed using error prone PCR or gene shuffling. In certain the mutation(s) in the global transcription machinery is/are one or more point mutations and/or one or more truncations or deletions, In some embodiments, the truncation does not include the promoter binding region of the global transcription machinery.

In some embodiments of the foregoing methods, the phenotype is increased tolerance of deleterious culture conditions. In other embodiments, the phenotype is solvent tolerance or hazardous waste tolerance, in which the solvent is, for example, ethanol, hexane or cyclohexane. In still other embodiments, phenotype is tolerance of industrial media.

In some embodiments of the foregoing methods, the phenotype is tolerance of high sugar concentration, tolerance of high salt concentration, tolerance of high temperatures, tolerance of extreme pH, or tolerance of surfactants. In certain embodiments, the phenotype is tolerance of a plurality of deleterious conditions.

In some embodiments of the foregoing methods, the phenotype is increased metabolite production, which in some embodiments is a non-native compound.

In some embodiments of the foregoing methods, the phenotype is tolerance to a toxic substrate, metabolic intermediate or product. In other embodiments, the phenotype is antibiotic resistance. In still other embodiments, the phenotype is increased growth, growth rate and/or survival relative to the unaltered or previously altered cell.

In some embodiments of the foregoing methods, the cell used in the method is optimized for the phenotype prior to mutating the global transcription machinery.

In some embodiments of the foregoing methods, the method also include identifying the changes in gene expression in the altered cell, which changes in gene expression optionally are determined using a nucleic acid microarray.

In some embodiments of the foregoing methods, the cell is not a *Lactobacillus* cell, but is for example, a cell of another bacterial species, e.g., *E. coli*.

According to another aspect of the invention, collections of cells produced by the foregoing methods are provided.

According to yet another aspect of the invention, methods for evaluating phenotypic diversity generated by global transcription machinery engineering are provided. The methods include providing one or more populations of cells that have been subjected to global transcription machinery engineering, measuring a phenotype of the one or more populations of cells and calculating average phenotypic distance for each population. The average phenotypic distance provides a measure of the phenotypic diversity generated by global transcription machinery engineering.

In some embodiments the global transcription machinery engineering includes mutating one or more transcription regulators. Preferably the mutations are made to a nucleic acid encoding the transcription regulator.

In other embodiments, the population of cells is produced by introducing into cells a plurality of mutated transcription regulators. Preferably the transcription regulators are one or more sigma factors. In some embodiments, the plurality of mutated transcription regulators is a library of mutated transcription regulators, preferably encoded by plasmids.

In further embodiments of the foregoing methods, the average phenotypic distance for each population is calculated under non-stressful conditions and stressful conditions, and the average phenotypic distances under the non-stressful conditions and the stressful conditions is compared to evaluate the phenotypic diversity generated by global transcription machinery engineering under the non-stressful conditions and the stressful conditions.

Preferred phenotypes include intracellular pH ($pH_i$), colony size or growth rate of the one or more populations of cells. In embodiments in which the phenotype is colony size, the colony size preferably is measured with image analysis software.

In still other embodiments of the foregoing methods, the average phenotypic distance is calculated using:

$$d = <d_{i,j}> \forall i,j$$

$$d_{i,j} = |P_i - P_j|$$

where the brackets indicate an average over the members of the population and $P_i$ is the phenotype of colony i. The average phenotypic distance also can be calculated using other non-Euclidean formulae. Preferably such non-Euclidean formulae calculate coefficient of variation or standard deviation.

In preferred embodiments, the foregoing methods include normalizing the average phenotypic distance by comparing the average phenotypic distance for each population to that of an unmutated control population. Preferably the average phenotypic distance is normalized by calculating a statistical distance measure. More preferably the statistical distance measure is Bhattacharyya distance.

The invention also provides methods for selecting a transcriptional regulator or a combinations of transcription regulators for strain improvement. The methods include evaluating phenotypic diversity generated by global transcription machinery engineering of the transcriptional regulator or the combinations of transcription regulators using the foregoing methods.

These and other aspects of the invention, as well as various embodiments thereof, will become more apparent in reference to the drawings and detailed description of the invention.

DETAILED DESCRIPTION OF THE INVENTION

Figure 1:
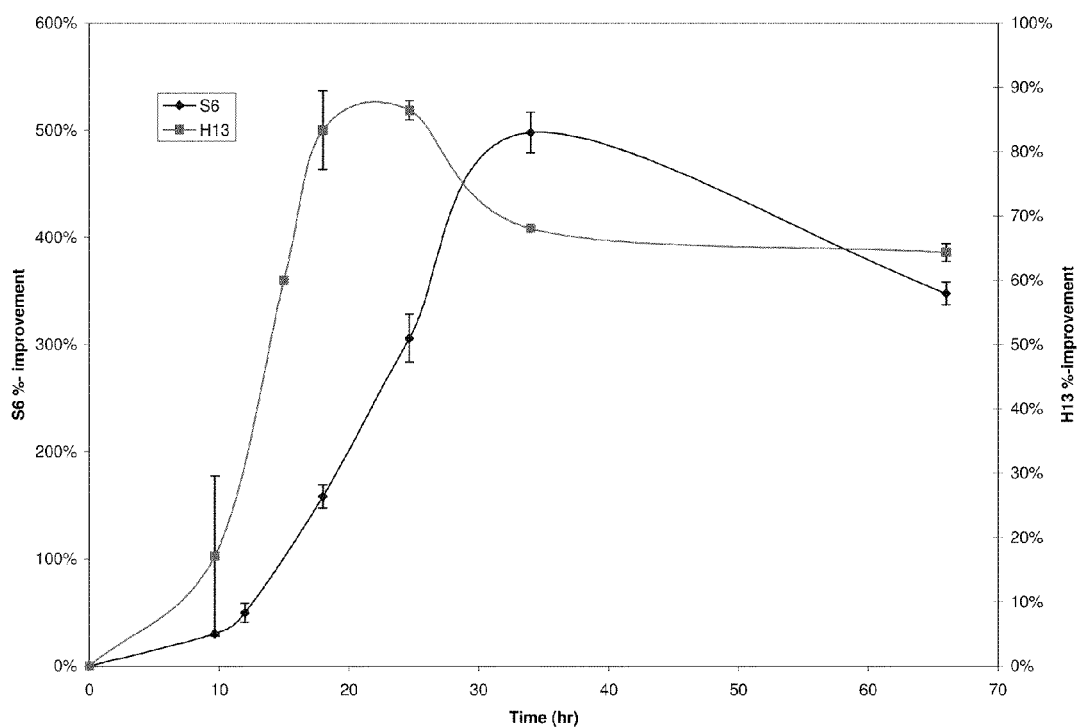
FIG. 1. The graph shows the percent improvement in optical density ($OD_{600}$) of strains bearing sigma factor mutants S6 and H13 compared to a strain bearing the control plasmid (pDK12D). Both curves reflect the improvement in the media used for selection, i.e., LA condition for S6 and HCl condition for H13 (See Materials and Methods). Note that the axes have different scales.

We engineered the principal sigma factor of *Lactobacillus plantarum* for improving its tolerance to high lactic acid and low pH conditions. These stresses present a challenge to commercial fermentations of lactate, a raw material in the production of biodegradable polymers and food additives (25). *Lactobacillus plantarum* grows optimally at pH 6.0, but the downstream separation is easiest at lower pH (near or below the pKa=3.85), at which more of the acid is undissociated (13, 27). A global approach seems ideal, as several genes mediate the response to acidic environments in both the presence and absence of lactate (4, 26).

Lactic and other organic acids are thought to hinder growth via different mechanisms. The toxicity is pronounced at low pH because only the protonated, uncharged form of the acid can cross freely through the membrane. In the cytoplasm, the acid dissociates following the Henderson-Hasselbach equation, lowering the cytoplasmic pH and increasing the concentration of the anionic species. This sequence of events results, first, in the partial dissipation of the proton gradient across the cell membrane, which leads to an energy shortage (19); second, in the buildup of protons in the cytoplasm, which affects its biochemical properties (6, 18); and third, in the intracellular accumulation of the anion and the consequent end-product inhibition, which plays a key role in toxicity in the case of lactic acid (26).

Novel mutants of the principal sigma factor (rpoD) of *Lactobacillus plantarum* are provided that confer improved tolerance to lactic acid and low pH. Sigma factor libraries were constructed by error-prone PCR (epPCR) and challenged in media acidified with either lactic or hydrochloric acids, and mutants S6 and H13 were isolated in those conditions respectively. Mutant H13 has the following nonsynonymous substitutions: A44T, K74R, A114D, A119S, and a base insertion that introduces a stop codon in position 120. The result is an N-terminal truncated protein that comprises the first 119 amino acids of the sigma factor. Mutants having one or more of the nonsynonymous substitutions and/or the truncation also are provided. Mutant S6 has a single nonsynonymous substitution Q345K, located in the region of the sigma subunit that binds to the −35 promoter box.

The pleiotropic nature of the Q345K mutation suggests that mutagenesis of the regions of rpoD that are in charge of promoter recognition may be very helpful in eliciting improved phenotypes. As such, the regions that contain the binding sites for the −10 promoter box (amino acids M155-Q228) and the −35 promoter box (amino acids G276-E368) can be engineered specifically. These regions are well conserved across many bacterial species, and the equivalent amino acids in the different sigma factors could be targets for transcriptional engineering in those species.

Using the invention, we exploit the global regulatory functions of the rpoD sigma factor to introduce multiple simultaneous gene expression changes and thus facilitate whole-cell engineering by selecting mutants responsible for improved cellular phenotype.

The invention provides methods for altering the phenotype of a cell. The methods include mutating a nucleic acid encoding a global transcription machinery protein and, optionally, its promoter, expressing the nucleic acid in a cell to provide an altered cell that includes a mutated global transcription machinery protein, and culturing the altered cell. As used herein, "global transcription machinery" is one or more molecules that modulates the transcription of a plurality of genes. The global transcription machinery can be proteins that affect gene transcription by interacting with and/or modulating the activity of a RNA polymerase molecule, including any subunit or transcription factor that binds to the RNA polymerase. The global transcription machinery also can be proteins that alter the ability of the genome of a cell to be transcribed (e.g., methyltransferases). Further, global transcription machinery can be molecules other than proteins (e.g., micro RNAs) that alter transcription of a plurality of genes. Other targets for global engineering include proteins or nucleic acids that regulate other cellular processes, such as translation or RNA degradation. These include other subunits of the RNA polymerase ($\alpha$, $\beta$, $\omega$, etc.), the degradosome (RNAses, PNPases, helicases, etc.), the ribosomal proteins or rRNAs, RNA-processing proteins (like Hfq), and similar molecules. Also, DNA-binding regions of other proteins (like activators or repressors) could similarly be targets for global engineering.

Global transcription machinery useful in accordance with the invention include bacterial sigma factors and anti-sigma factors. Exemplary genes that encode sigma factors include rpoD (encoding the principal sigma factor), rpoF, rpoS, rpoH, rpoN, rpoE, fecI and sigH. Anti-sigma factors bind to the sigma factors and control their availability and consequently transcription. The anti-sigma factors can be mutated to control their impact in transcription for normal cells. In addition, novel pairings of mutant sigma factors with mutant anti-sigma factors can be created to create further control of transcription in cells. For example, the anti-sigma factor can be expressed using an inducible promoter, which allows for tunable control of the phenotype imparted by the mutant sigma factor.

Global transcription machinery also includes polypeptides that alter the ability of chromosomal DNA to be transcribed, such as nucleic acid methyltransferases (e.g., DamMT, DNMT1, Dnmt3a).

In many instances, the process of mutating the global transcription machinery will include iteratively making a plurality of mutations of the global transcription machinery, but it need not, as even a single mutation of the global transcription machinery can result in dramatic alteration of phenotype, as is demonstrated herein.

While the methods of the invention typically are carried out by mutating the global transcription machinery followed by introducing the mutated global transcription machinery into a cell to create an altered cell, it is also possible to mutate endogenous global transcription machinery genes, e.g., by replacement with mutant global transcription machinery or by in situ mutation of the endogenous global transcription machinery. As used herein, "endogenous" means native to the cell; in the case of mutating global transcription machinery, endogenous refers to the gene or genes of the global transcription machinery that are in the cell. In contrast, the more typical methodology includes mutation of a global transcription machinery gene or genes outside of the cell, followed by introduction of the mutated gene(s) into the cell.

The global transcription machinery genes can be of the same species or different species as the cell into which they are introduced. Examples of the former are described herein. Examples of the latter include, for example, mutating *E. coli* sigma factor 70 (rpoD) and introducing it into *Lactobacillus* to alter the phenotype of the *Lactobacillus* cells. Other global transcription machinery of *E. coli* also could be used in the same fashion. The different global transcription machinery also could be sourced from different kingdoms or phyla of organisms. Depending on the method of mutation used, same and different global transcription machinery can be combined for use in the methods of the invention, e.g., by gene shuffling. Likewise, the cell into which the sigma factor is introduced can be other bacterial species (e.g., *E. coli*).

Optionally, the transcriptional control sequences of global transcription machinery can be mutated, rather than the coding sequence itself. Transcriptional control sequences include promoter and enhancer sequences. The mutated promoter and/or enhancer sequences, linked to the global transcription machinery coding sequence, can then be introduced into the cell.

After the mutant global transcription machinery is introduced into the cell to make an altered cell, then the phenotype of the altered cell is determined/assayed. This can be done by selecting altered cells for the presence (or absence) of a particular phenotype. Examples of phenotypes are described in greater detail below. The phenotype also can be determined by comparing the phenotype of the altered cell with the phenotype of the cell prior to alteration.

In preferred embodiments, the mutation of the global transcription machinery and introduction of the mutated global transcription machinery are repeated one or more times to produce an "$n^{th}$ generation" altered cell, where "n" is the number of iterations of the mutation and introduction of the global transcription machinery. For example, repeating the mutation and introduction of the global transcription machinery once (after the initial mutation and introduction of the global transcription machinery) results in a second generation altered cell. The next iteration results in a third generation altered cell, and so on. The phenotypes of the cells containing iteratively mutated global transcription machinery then are determined (or compared with a cell containing non-mutated global transcription machinery or a previous iteration of the mutant global transcription machinery) as described elsewhere herein.

The process of iteratively mutating the global transcription machinery allows for improvement of phenotype over sequential mutation steps, each of which may result in multiple mutations of the global transcription machinery. It is also possible that the iterative mutation may result in mutations of particular amino acid residues "appearing" and "disappearing" in the global transcription machinery over the iterative process.

In a typical use of the methodology, the global transcription machinery is subjected to directed evolution by mutating a nucleic acid molecule that encodes the global transcription machinery. A preferred method to mutate the nucleic acid molecule is to subject the coding sequence to mutagenesis, and then to insert the nucleic acid molecule into a vector (e.g., a plasmid). This process may be inverted if desired, i.e., first insert the nucleic acid molecule into a vector, and then subject the sequence to mutagenesis, although it is preferred to mutate the coding sequence prior to inserting it in a vector.

When the directed evolution of the global transcription machinery is repeated, i.e., in the iterative processes of the invention, a preferred method includes the isolation of a nucleic acid encoding the mutated global transcription machinery and optionally, its promoter, from the altered cell. The isolated nucleic acid molecule is then mutated (producing a nucleic acid encoding a second generation mutated global transcription machinery), and subsequently introduced into another cell.

The isolated nucleic acid molecule when mutated, forms a collection of mutated nucleic acid molecules that have different mutations or sets of mutations. For example, the nucleic acid molecule when mutated randomly can have set of mutations that includes mutations at one or more positions along the length of the nucleic acid molecule. Thus, a first member of the set may have one mutation at nucleotide n1 (wherein nx represents a number of the nucleotide sequence of the nucleic acid molecule, with x being the position of the nucleotide from the first to the last nucleotide of the molecule). A second member of the set may have one mutation at nucleotide n2. A third member of the set may have two mutations at nucleotides n1 and n3. A fourth member of the set may have two mutations at positions n4 and n5. A fifth member of the set may have three mutations: two point mutations at nucleotides n4 and n5, and a deletion of nucleotides n6-n7. A sixth member of the set may have point mutations at nucleotides n1, n5 and n8, and a truncation of the 3' terminal nucleotides. A seventh member of the set may have nucleotides n9-n10 switched with nucleotides n11-n12. Various other combinations can be readily envisioned by one of ordinary skill in the art, including combinations of random and directed mutations.

The collection of nucleic acid molecules can be a library of nucleic acids, such as a number of different mutated nucleic acid molecules inserted in a vector. Such a library can be stored, replicated, aliquoted and/or introduced into cells to produce altered cells in accordance with standard methods of molecular biology.

Mutation of the global transcription machinery for directed evolution preferably is random. However, it also is possible to limit the randomness of the mutations introduced into the global transcription machinery, to make a non-random or partially random mutation to the global transcription machinery, or some combination of these mutations. For example, for a partially random mutation, the mutation(s) may be confined to a certain portion of the nucleic acid molecule encoding the global transcription machinery.

The method of mutation can be selected based on the type of mutations that are desired. For example, for random mutations, methods such as error-prone PCR amplification of the nucleic acid molecule can be used. Site-directed mutagenesis can be used to introduce specific mutations at specific nucleotides of the nucleic acid molecule. Synthesis of the nucleic acid molecules can be used to introduce specific mutations and/or random mutations, the latter at one or more specific nucleotides, or across the entire length of the nucleic acid molecule. Methods for synthesis of nucleic acids are well known in the art (e.g., Tian et al., *Nature* 432: 1050-1053 (2004)).

DNA shuffling (also known as gene shuffling) can be used to introduce still other mutations by switching segments of nucleic acid molecules. See, e.g., U.S. Pat. No. 6,518,065, related patents, and references cited therein. The nucleic acid molecules used as the source material to be shuffled can be nucleic acid molecule(s) that encode(s) a single type of global transcription machinery (e.g., rpoD), or more than one type of global transcription machinery. For example, nucleic acid molecules encoding different global transcription machinery, such as different sigma factors of a single species (e.g., rpoD and rpoN) can be shuffled. Likewise, nucleic acid molecules encoding different types of global transcription machinery, e.g., rpoD and a non-sigma factor, can be shuffled.

A variety of other methods of mutating nucleic acid molecules, in a random or non-random fashion, are well known to one of ordinary skill in the art. One or more different methods can be used combinatorially to make mutations in nucleic acid molecules encoding global transcription machinery. In this aspect, "combinatorially" means that different types of mutations are combined in a single nucleic acid molecule, and assorted in a set of nucleic acid molecules. Different types of mutations include point mutations, truncations of nucleotides, deletions of nucleotides, additions of nucleotides, substitutions of nucleotides, and shuffling (e.g., re-assortment) of segments of nucleotides. Thus, any single nucleic acid molecule can have one or more types of mutations, and these can be randomly or non-randomly assorted in a set of nucleic acid molecules. For example, a set of nucleic acid molecules can have a mutation common to each nucleic acid molecule in the set, and a variable number of mutations that are not common to each nucleic acid molecule in the set. The common mutation, for example, may be one that is found to be advantageous to a desired altered phenotype of the cell.

In some embodiments a promoter binding region of the global transcription machinery is not disrupted or removed by the one or more truncations or deletions.

The mutated global transcription machinery can exhibit increased or decreased transcription of genes relative to the unmutated global transcription machinery. In addition, the mutated global transcription machinery can exhibit increased or decreased repression of transcription of genes relative to the unmutated global transcription machinery.

As used herein, a "vector" may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to plasmids and phagemids.

A cloning vector is one which is able to replicate autonomously or integrated in the genome in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase.

An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase, luciferase or alkaline phosphatase), and genes which visibly affect the phenotype of transformed or transfected cells, hosts, colonies or plaques (e.g., green fluorescent protein). Preferred vectors are those capable of autonomous replication and expression of the structural gene products present in the DNA segments to which they are operably joined.

As used herein, a coding sequence and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CAAT sequence, and the like. In particular, such 5' non-transcribed regulatory sequences will include a promoter region which includes a promoter sequence for transcriptional control of the operably joined gene. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art.

Expression vectors containing all the necessary elements for expression are commercially available and known to those skilled in the art. See, e.g., Sambrook et al., *Molecular Cloning: A Laboratory Manual*, Second Edition, Cold Spring Harbor Laboratory Press, 1989. Cells are genetically engineered by the introduction into the cells of heterologous DNA (RNA) encoding a global transcription machinery polypeptide or fragment or variant thereof. That heterologous DNA (RNA) is placed under operable control of transcriptional elements to permit the expression of the heterologous DNA in the host cell.

When the nucleic acid molecule that encodes mutated global transcription machinery is expressed in a cell, a variety of transcription control sequences (e.g., promoter/enhancer sequences) can be used to direct expression of the global transcription machinery. The promoter can be a native promoter, i.e., the promoter of the global transcription machinery gene, which provides normal regulation of expression of the global transcription machinery. A variety of conditional promoters also can be used, such as promoters controlled by the presence or absence of a molecule.

A nucleic acid molecule that encodes mutated global transcription machinery can be introduced into a cell or cells using methods and techniques that are standard in the art. For example, nucleic acid molecules can be introduced by various transfection methods, transduction, electroporation, particle bombardment, etc.

Expressing the nucleic acid molecule encoding mutated global transcription machinery also may be accomplished by integrating the nucleic acid molecule into the genome or by replacing a nucleic acid sequence that encodes the endogenous global transcription machinery.

By mutating global transcription machinery, novel compositions are provided, including nucleic acid molecules encoding global transcription machinery produced by one or more rounds of mutation. The rounds of mutation can include directed evolution, in which each round of mutation is followed by a selection process to select the mutated global transcription machinery that confer a desired phenotype. The methods of mutation and selection of the mutated global transcription machinery are as described elsewhere herein. Global transcription machinery produced by these nucleic acid molecules also are provided.

In certain cases, it has been found that mutated global transcription machinery are truncated forms of the unmutated global transcription machinery. In particular, for rpoD, it has been found that a carboxyl-terminal truncation of rpoD that leaves only the amino-terminus of the rpoD protein confers advantageous phenotypes to bacteria in which it is introduced. Thus, fragments of global transcription machinery are provided, more particularly fragments of rpoD. Nucleic acid molecules encoding the truncated global transcription machinery also are provided, including nucleic acid molecules as contained in vectors and/or cells.

The invention is exemplified using *L. plantarum*. Other *Lactobacillus* species useful in the invention include *L. acidophilus, L. delbrueckii, L. helveticus, L. salivarius, L. casei, L. curvatus, L. sakei, L. brevis, L. buchneri, L. fermentum*, and *L. reuteri*. Likewise, other bacterial species and other microorganisms can be used.

Mutation of global transcription machinery (e.g., by error-prone PCR or directed evolution) produces altered cells, some of which have altered phenotypes. Thus the invention also includes selecting altered cells for a predetermined phenotype or phenotypes. Selecting for a predetermined phenotype can be accomplished by culturing the altered cells under selective conditions. Selecting for a predetermined phenotype also can be accomplished by high-throughput assays of individual cells for the phenotype. For example, cells can be selected for tolerance to deleterious conditions and/or for increased production of metabolites. Selection for increased growth also is exemplified.

A wide variety of phenotypes can be selected in accordance with the invention. In some preferred embodiments, the phenotype is increased tolerance of deleterious culture conditions. Such phenotypes include: solvent tolerance or hazardous waste tolerance, e.g., solvents such as ethanol, and organic solvents such as hexane or cyclohexane; tolerance of metabolites such as lactate; tolerance of industrial media; tolerance of high sugar concentration; tolerance of high salt concentration; tolerance of high temperatures; tolerance of extreme pH conditions (high or low); tolerance of surfactants, e.g., detergents such as sodium dodecyl sulfate (SDS); and tolerance of a plurality of deleterious conditions.

Other tolerance phenotypes include tolerance of osmotic stress, tolerance to a toxic substrate, metabolic intermediate or product. Toxic metabolites include organic solvents, acetate, para-hydroxybenzoic acid (pHBA), para-hydroxycinnamic acid, hydroxypropionaldehyde, and overexpressed proteins. Additional phenotypes include increased antibiotic resistance and resistance to apoptosis.

As used herein with respect to altered cells containing mutated global transcription machinery, "tolerance" means that an altered cell is able to withstand the deleterious conditions to a greater extent than an unaltered cell, or a previously altered cell. For example, the unaltered or previously altered cell is a "parent" of the "child" altered cell, or the unaltered or previously altered cell is the $(n-1)^{th}$ generation as compared to the cell being tested, which is $n^{th}$ generation. "Withstanding the deleterious conditions" means that the altered cell has increased growth, growth rate and/or survival relative to the unaltered or previously altered cell. This concept also includes increased production of metabolites that are toxic to cells.

With respect to tolerance of lactic acid concentrations, such concentrations can be $\geq 1$ g/L, $\geq 2$ g/L, $\geq 3$ g/L, $\geq 3.5$ g/L, $\geq 4$ g/L, $\geq 4.5$ g/L, $\geq 5$ g/L, $\geq 5.5$ g/L, $\geq 6$ g/L of L-lactate, etc. With respect to tolerance of high salt concentrations, such concentrations can be $\geq 1$ M, $\geq 2$ M, $\geq 3$ M, $\geq 4$ M, $\geq 5$ M, etc. With respect to tolerance of high temperatures, the temperatures can be, e.g., $\geq 42°$ C., $\geq 44°$ C., $\geq 46°$ C., $\geq 48°$ C., $\geq 50°$ C. for bacterial cells. With respect to tolerance of extreme pH, exemplary low pH cutoffs include, e.g., $\leq$pH4.0, $\leq$pH3.85, $\leq$pH3.5, $\leq$pH3.0, $\leq$pH2.0, $\leq$pH1.0, and exemplary high pH cutoffs include, e.g., $\geq$pH10, $\geq$pH11, $\geq$pH12, $\geq$pH13. With respect to tolerance of surfactants, exemplary surfactant concentrations are $\geq 5\%$ w/v, $\geq 6\%$ w/v, $\geq 7\%$ w/v, $\geq 8\%$ w/v, $\geq 9\%$ w/v, $\geq 10\%$ w/v, $\geq 12\%$ w/v, $\geq 15\%$ w/v, etc. With respect to tolerance of ethanol, exemplary ethanol concentrations are ≧4% v/v, ≧5% v/v, ≧6% v/v, ≧7% v/v, ≧8% v/v, ≧9% v/v, ≧10% v/v, etc. With respect to tolerance of osmotic stress, exemplary concentrations that induce osmotic stress are ≧100 mM, ≧150 mM, ≧200 mM, ≧250 mM, ≧300 mM, ≧350 mM, ≧400 mM, etc. In addition, many other stresses, like solvents or toxic substrates, are known to the skilled person.

The invention includes obtaining increased production of metabolites by cells. As used herein, a "metabolite" is any molecule that is made or can be made in a cell. Metabolites include metabolic intermediates or end products, any of which may be toxic to the cell, in which case the increased production may involve tolerance of the toxic metabolite. Thus metabolites include small molecules, peptides, large proteins, lipids, sugars, etc.

Metabolites can be native to the cells used or can be non-native compounds. In the latter case, increased production can be achieved, e.g., by introducing heterologous genes that cause production of the non-native metabolite to a strain, and in this strain increasing the level of production further with a mutagenized sigma factor. Also, the production of a precursor metabolite can be optimized first using transcriptional engineering approaches, and then the genes that convert the precursor to the final molecule can be introduced into the production strain.

Exemplary metabolites include the metabolite demonstrated in the working examples (lactate), a lactate metabolite (e.g., a metabolic derivative of lactate resulting from metabolic processing of lactate, such as a downstream metabolite of lactate) or a lactate intermediate (e.g., a metabolic precursor of lactate). Thus, in these particular nonlimiting embodiments, metabolites include lactate or any metabolite upstream or downstream of lactate in the lactate metabolic pathway.

The invention also includes culturing cells in a low pH culture medium, e.g., lower pH than otherwise optimal or tolerated by the cells, as a result of the change(s) made to the cells as are described herein. Conducting fermentations at low pH is an advantage, regardless of the product, because it provides a safeguard against contamination by opportunistic microorganisms. For example, low pH of the culture medium can be obtained by acidifying the culture medium with an acid, which may be added or the result of the culturing process itself. Exemplary acids include lactic acid and hydrochloric acid; other acids applicable in these embodiments will be known to the skilled person.

The invention also provides for selecting for a plurality of phenotypes, such as tolerance of a plurality of deleterious conditions, increased production of a plurality of metabolites, or a combination of these. An example of this is the multiple tolerance of high lactic acid and low pH by *L. plantarum* demonstrated in the working examples.

It may be advantageous to use cells that are previously optimized for the predetermined phenotype prior to introducing mutated global transcription machinery. Thus, in the production of lactate, for example, rather than starting with a bacterial cell that produces only a small amount of lactate, one preferentially uses a cell that produces a higher amount of lactate, more preferably an optimized amount of lactate. In such cases, the mutated global transcription machinery is used to further improve an already-improved phenotype.

Via the actions of the mutated global transcription machinery, the altered cells will have altered expression of genes. The methods of the invention can, in certain aspects, include identifying the changes in gene expression in the altered cell. Changes in gene expression can be identified using a variety of methods well known in the art. Preferably the changes in gene expression are determined using a nucleic acid microarray. The invention can be used as the main source of information about a certain phenotype, and thus can be utilized as a tool for functional genomics. For example, a mutated global regulator is first selected for an improved phenotype, and microarray or similar analyses on this improved strain can be used to find the genes are responsible for the improved phenotype.

In some aspects of the invention, one or more of the changes in gene expression that are produced in a cell by mutated global transcription machinery can be reproduced in another cell in order to produce the same (or a similar) phenotype. The changes in gene expression produced by the mutated global transcription machinery can be identified as described above. Individual gene(s) can then be targeted for modulation, through recombinant gene expression or other means. For example, mutated global transcription machinery may produce increases in the expression of genes A, B, C, D, and E, and decreases in the expression of genes F, G, and H. The invention includes modulating the expression of one or more of these genes in order to reproduce the phenotype that is produced by the mutated global transcription machinery. To reproduce the predetermined phenotype, one or more of genes A, B, C, D, E, F, G, and H can be increased, e.g., by introducing into the cell expression vector(s) containing the gene sequence(s), increasing the transcription of one or more endogenous genes that encode the one or more gene products, or by mutating a transcriptional control (e.g., promoter/enhancer) sequence of the one or more genes, or decreased, e.g., by mutating one or more genes that encode the one or more gene products or a transcriptional control (e.g., promoter/enhancer) sequence of the one or more genes.

Optionally, the changes in gene expression in the cell containing the mutated global transcription machinery are used to construct a model of a gene or protein network, which then is used to select which of the one or more gene products in the network to alter. Models of gene or protein networks can be produced via the methods of Ideker and colleagues (see, e.g., Kelley et al., *Proc Natl Acad Sci USA* 100(20), 11394-11399 (2003); Yeang et al. *Genome Biology* 6(7), Article R62 (2005); Ideker et al., *Bioinformatics*. 18 Suppl 1:S233-40 (2002)) or Liao and colleagues (see, e.g., Liao et al., *Proc Natl Acad Sci USA* 100(26), 15522-15527 (2003); Yang et al., *BMC Genomics* 6, 90 (2005)), The invention also includes cells produced by any of the methods described herein. The cells are useful for a variety of purposes, including: industrial production of molecules (e.g., lactate).

In another aspect, the invention provides methods for altering the production of a metabolite. The methods include mutating global transcription machinery to produce an altered cell, in accordance with the methods described elsewhere herein. The cell preferably is a cell that produces a selected metabolite as described above, and as described above, preferably is previously optimized for production of the metabolite. Altered cells that produce increased or decreased amounts of the selected metabolite can then be isolated. The methods also can include culturing the isolated cells and recovering the metabolite from the cells or the cell culture. The steps of culturing cells and recovering metabolite can be carried out using methods well known in the art. Various preferred cell types, global transcription machinery and metabolites are provided elsewhere herein.

The invention also provides collections of nucleic acid molecules, which may be understood in the art as a "library" of nucleic acid molecules using the standard nomenclature of molecular biology. Such collections/libraries include a plurality of different nucleic acid molecule species, with each nucleic acid molecule species encoding global transcription machinery that has different mutation(s) as described elsewhere herein.

Other collections/libraries of the invention are collections/libraries of cells that include the collections/libraries of nucleic acid molecules described above. The collections/libraries include a plurality of cells, with each cell of the plurality of cells including one or more of the nucleic acid molecules. The cell types present in the collection are as described elsewhere herein, and include single cells as well as multicellular organisms that include one or more of such cells. In the libraries of cells, the nucleic acid molecules can exist as extrachromosomal nucleic acids (e.g., on a plasmid), can be integrated into the genome of the cells, and can replace nucleic acids that encode the endogenous global transcription machinery.

The collections/libraries of nucleic acids or cells can be provided to a user for a number of uses. For example, a collection of cells can be screened for a phenotype desired by the user. Likewise, a collection of nucleic acid molecules can be introduced into a cell by the user to make altered cells, and then the altered cells can be screened for a particular phenotype(s) of interest. For example, to use a phenotype described herein, a user seeking to increase lactate production and possessing a bacterial strain that produces a certain amount of lactate could introduce a collection of mutated global transcriptions factor(s) into the bacterial strain, and then screen for improved production of lactate. Subsequent rounds of directed evolution by mutation and reintroduction of the global transcription machinery also can be carried out to obtain further improvements in lactate production.

Collections/libraries can be stored in containers that are commonly used in the art, such as tubes, microwell plates, etc.

In addition to addressing the problems of environmental tolerance in *Lactobacillus*, the invention provides a platform for analyzing the future prospects of the present and similar technologies. Engineering of the transcription machinery opened the possibility of exploring other global regulators to influence the internal environment of the cell through different processes. The number of regulators increases considerably from prokaryotes to eukaryotes, being very large in mammals (8). Given the versatility of these libraries, a method for assessing their potential would facilitate prioritization in screening them, saving time and resources. Furthermore, if combinations of regulators are considered, such an assessment tool can reduce the number of choices significantly.

From an evolutionary viewpoint, the potential of a strain improvement method is related to how effective it is for exploring the phenotypic space. This aspect can be measured using population diversity. Strictly, one should measure the diversity of a sigma factor library at the transcriptomic level, but high-throughput analysis of the mRNA profile for thousands of samples is technologically unavailable. Alternatively, one may focus in diversity directly at the phenotypic level. This is an acceptable approximation as (i) it can be assumed that the phenotypic landscape as a function of the transcriptome is not perfectly flat, and (ii) we are more interested in feasible phenotypes than in feasible transcriptomes.

A quantification method has been also described for assessing the potential of different libraries for phenotype improvement. Any phenotype (e.g., growth rate under different conditions, metabolite production, internal pH, etc.) that can be assayed with a high-throughput screen can be used for quantification of phenotypic distance. For example, the intracellular pH ($pH_i$) is a complex trait that can be used, as it is affected by the relative levels of proteins and metabolites in the cell (33), and is expected to vary with changes in the transcriptome. In addition, $pH_i$ is readily probed for individual cells using flow cytometry (34, 35).

The phenotype may be complex (such as those previously mentioned), but is not necessarily complex. For example, if one would want to quantify the variability of a promoter library that expresses green fluorescent protein, then the phenotypic value could be, for instance, fluorescence intensity. In other words, this method is useful generally to evaluate any library with a quantifiable phenotype, though high-throughput is preferred for practicability. The phenotype being measured is used to calculate the average phenotypic distance using, $$d = <d_{i,j}> \forall i,j$$

$$d_{i,j} = |P_i - P_j|$$

The value of d can be bootstrapped to find the distribution of its value. For normalization, statistical distance measures are used to subtract the distance value of a control population from that of the library population. The Bhattacharyya distance is an example of such a statistical distance measure.

This procedure can be used to compare the potential of libraries of different regulators (e.g., sigma S vs. Sigma D factors), different mutagenesis targets (−10 vs. −35 binding regions as described above), the effect on phenotype of different conditions, etc.

As an example of this approach, we chose colony size under different conditions, related to growth rate, as the complex phenotype used to quantify diversity. The average phenotypic distance between members of a population was used to measure relative dissimilarity and to quantify the dimensions of the search space available to the population. When properly normalized, this distance reflects the divergence of a library (of a sigma factor or otherwise) with respect to the unmutated control. We apply this method for exploring the effect of mutation frequency of the sigma factor in phenotypic diversity, and to compare sigma factor libraries to those prepared by NTG-mutagenesis. The method can be readily generalized to other phenotypes and libraries.

EXAMPLES

Materials and Methods

Reagents and enzymes. Restriction enzymes, Antarctic phosphatase, and Phusion DNA polymerase were obtained from New England Biolabs (Ipswich, Mass.). Chloramphenicol, lysozyme, mutanolysin, penicillin G, and lactic acid were from Sigma-Aldrich (St. Louis, Mo.). Primers were designed with Vector NTI (version 10.1.1) and ordered from Invitrogen (Carlsbad, Calif.). Fastlink ligase was from Epicentre Biotechnologies (Madison, Wis.). For error-prone PCR (epPCR), the GeneMorph II Kit from Stratagene (La Jolla, Calif.) was used according to manufacturer's instructions.

Bacterial strains, plasmids and growth conditions. *L. plantarum* was obtained from ATCC (BAA-793) and *E. coli* DH5α from Invitrogen. *Lactobacillus* was routinely grown in MRS (bioMerieux, France) medium and *E. coli* in LB (Difco, Sparks, Md.). Media was supplemented with chloramphenicol to 8 µg/mL for *Lactobacillus* and 5 µg/mL for *E. coli* as needed. Plasmid pGK12 (18), obtained from Todd R. Klaenhammer, confers erythromycin and chloramphenicol resistance and was propagated unmethylated in *E. coli* GM1829. Plasmid pDK12 was constructed by inserting the multiple cloning site (MCS) of plasmid pUC18 into the NsiI and ClaI sites of pGK12. Primers MCSs and MCSa (Table 1) were used to amplify the MCS, the PCR product was cut along with pGK12 and the two fragments were ligated. The new plasmid (pDK12) is capable of alpha-complementation in DH5α. The control plasmid, PDK12D, has the unmutated rpoD gene amplified from *L. plantarum* genomic DNA ((17); NCBI Accession No. AL935257, region 219202-220308) with primers Xma-rpoprom and Xba-rpoterm. The reverse primer includes the transcriptional terminator of the pln operon (NCBI Accession No. X94434). The insert and pDK12 were cut with XmaI and XbaI and ligated. The correct structure of pDK12D was confirmed by sequencing.

until it reached ~0.5 (usually 2.5 hr after penicillin addition), and the culture was immediately placed on ice. All subsequent steps were done at 4° C. The chilled cells were centrifuged once for 5 min at 1500×g, washed twice with 3.5×EB (Sucrose 1M, $MgCl_2$, 3.5 mM) and then resuspended in 1/100 of the original culture volume. Electroporation was done in a Gene Pulser (Bio-Rad Laboratories, Hercules, Calif.) at 2.5 kV and 100 W, using a 0.2 cm cuvette. Immediately after the pulse, cells were resuspended in 1 mL MRSSM (MRS media

TABLE 1

Primers used.

| Name | Sequence (5' → 3') | SEQ ID NO |
|---|---|---|
| MCSs | gcgcgcatcgattgagtgagctgataccgctcgcc | 1 |
| MCSa | gcgcatgcatcgtcagcgggtgttggcg | 2 |
| Xma-rpoprom | gcgccccgggtttggttcagcagttaacgttggc | 3 |
| Xba-rpoterm | gcgctctagaaaaatagcccaaaacctcgttagga gattttgggctattttatcgatggttagtcagacgtcatcatctggtgattat | 4 |
| Asc-H13s | ggcgcgcctttggttcagcagttaacgttggc | 5 |
| H13a | taaaacgacggccagtgccaag | 6 |
| Asc-S6a | ggcgcgccaaaatagcccaaaacctcgttaggagatt | 7 |
| S6s | aggaaacagctatgacatgattacgaattc | 8 |
| pGK12s | tacttttacagtcggttttctaatgtcactaacct | 9 |
| pGK12a | aattgacgatttaaacaatattagctttgaacaatt | 10 |

To co-express the rpoD mutants, we fused them into the same plasmid. They were amplified with either Asc-H13s and H13a or with Asc-S6a and S6s primers so that each was expressed from its own promoter. The first insert was cut with XmaI and AscI and the second with AscI and XbaI. Cut inserts were simultaneously ligated to cut pDK12 and then electroporated into *Lactobacillus*. The correct structure was confirmed by PCR and sequencing with primers pGK12s and pGK12a, located in pDK12 external to the insertion site.

DNA extraction and purification. For plasmid extraction, the QIAprep kit (Qiagen, Valencia, Calif.) was used for both *Lactobacillus* and *E. coli*, except that for *Lactobacillus* the overnight culture (5 mL) was first washed with EDTA buffer (50 mM pH 8.0), resuspended in the same (2.4 mL) and lysozyme and mutanolysin were added to a final concentration of 2 mg/mL and 42 U/mL, respectively. The mixture was incubated for at least 1 hr at 37° C. with shaking, and then the plasmid prep protocol was followed using this mixture. Genomic DNA from *L. plantarum* was obtained using an UltraClean microbial DNA isolation kit (Mo Bio Laboratories, Carlsbad, Calif.) with no pretreatment of the culture. PCR products were purified using the QIAquik kit (Qiagen, Valencia, Calif.) prior to restriction and ligation reactions. Gel purification of the products of epPCR was done using a GeneClean kit (Qbiogene, Morgan Irvine, Calif.).

Transformation by electroporation. Transformation efficiency is a key determinant of library size. Therefore, an electroporation protocol previously described (3, 29) was optimized prior to library construction. An overnight culture was diluted (1:50) in fresh MRS, incubated with shaking at 37° C., and penicillin was added to a final concentration of 10 µg/mL after 1 hr of inoculation. The $OD_{600}$ was monitored supplemented with 1 M sucrose and 100 mM $MgCl_2$), grown for 2 hr at 37° C. with shaking, and plated in MRS agar with 8 µg/mL chloramphenicol.

Library construction and phenotype selection. Plasmid pDK12D was used as the template for the epPCR reaction, using primers Xma-rpoprom and Xba-rpoterm. Mutation frequency was varied by using different amounts of target; 560 ng for low, 280 ng for medium, and 28 ng for high, as suggested by the manufacturer. The inserts were cut with XmaI and XbaI, gel-purified, and inserted into linearized and dephosphorylated pDK12. The ligation reaction was electroporated into freshly prepared electrocompetent cells as described above. After overnight incubation, the colonies were scraped off from the plates and the liquid libraries were stored at −80° C. until phenotype selection. The total library size was >$10^5$. The NTG library was prepared from an unmutated strain as previously described (21).

Each library was challenged either in 5.5 g/L of L-lactate at an initial pH of 4.60±0.05 (LA condition) or at an initial pH of 3.85±0.05 (~$pK_a$) adjusted with HCl without added lactate (HCl condition). The pH was measured using a Symphony pH meter (VWR, West Chester, Pa.). Libraries were subcultured twice 20-30 hr after inoculation, and then plated to isolate individual clones. The plasmids carrying the mutant sigma factors were extracted, retransformed into fresh cells by electroporation, and the phenotypes were confirmed using the same conditions used for challenging.

Diversity quantification. Colony area was measured by plating cells in one of four conditions (all in MRS agar with chloramphenicol): 900 mM NaCl (high osmotic pressure), 60 mM HCl, 4 g/L L-lactate, or no stress. Cells were diluted and plated in low enough concentration to be able to distinguish individual clones. Plates were put at 4° C. overnight to stop growth before photographing using an AlphaImager 3400 system (Alpha Innotech, San Leandro, Calif.). Images were processed using MetaMorph version 6.2 (Molecular Devices, Sunnyvale, Calif.). All data analysis was done with MATLAB (MathWorks, Natick, Mass.). Average phenotypic (Euclidean) distance was calculated as $$d = \langle d_{i,j} \rangle \forall i,j$$

$$d_{i,j} = |P_i - P_j| \quad \text{(Eq. 1)}$$

where the brackets indicate an average over the members of the population and $P_i$ is the phenotype of colony i. In this case, the logarithm of the colony area, A, was used as it is more physiologically meaningful than the area in assessing a measure of the growth rate:

$$P_i = \ln A_i \quad \text{(Eq. 2)}$$

Bootstrapping (11) was used to find the distribution of the average phenotypic distance (d). This algorithm involves re-sampling (with replacement) the population and calculating the value of d every time. Thus, the result is easily displayed in a histogram that reflects the probability that d has a certain value.

For the clustering analysis, a silhouette value was calculated for each object i using $$S_i = \frac{b_i - a_i}{\max\{a_i, b_i\}} \quad \text{(Eq. 3)}$$

where $b_i$ is the minimum of the average distances of object i to all objects in other clusters and $a_i$ is the average distance of object i to objects in the same cluster (in this case, object i is the value $P_i$ for colony i and a cluster is a group of colonies that have similar values of $P_i$). The silhouette value expressed in this form ranges from −1 (for misplaced objects) to +1 (for accurately placed objects).

The Bhattacharyya distance (BD) was used to normalize the average phenotypic distances of the libraries with that of the control. The BD was used because, as a result of the bootstrapping algorithm, the average phenotypic distance for each population is not a single value, but a distribution of values. Therefore, both the mean and variance of this distribution must be used. The BD was computed according to (15)

$$BD = \frac{1}{8}(\mu_l - \mu_c)^T \left(\frac{\Sigma_l + \Sigma_c}{2}\right)^{-1} (\mu_l - \mu_c) + \frac{1}{2}\ln\left(\frac{\left|\frac{\Sigma_l + \Sigma_c}{2}\right|}{\sqrt{|\Sigma_l||\Sigma_c|}}\right) \quad \text{(Eq. 4)}$$

Where $\Sigma$ is the covariance matrix, $\mu$ is the mean vector, and the subscripts l and c are for the library and control populations.

Fermentations. Overnight cultures of each clone were diluted in shake-flasks to an $OD_{600}$=0.02 in either MRS supplemented with glucose to 100 g/L (pH not adjusted) or MRS with no added glucose and initial pH adjusted to 3.85±0.05 with HCl (same as HCl condition described previously). Glucose supplementation was necessary to ensure that this nutrient was not limiting, following previously established practices (14, 26). L-lactate in the supernatant was measured with a YSI 2700 Select Biochemistry Analyzer (YSI, Yellow Springs, Ohio).

Results

Isolation of Improved Sigma Factor Mutants in High Lactic Acid and Low pH.

Given that lactic acid fermentations at low pH are characterized by high concentrations of free acid and protons, both conditions were explored. First, we constructed libraries of the principal sigma factor by error prone PCR. Different mutation frequencies (low, medium, and high) were achieved by varying the amount of template DNA in the reaction. Then, we challenged these libraries either in 5.5 g/L of L-lactate at an initial pH=4.6 (LA condition) or at an initial pH of 3.85 adjusted with inorganic acid (HCl condition). The LA condition addresses the end-product inhibition aspect of the stress directly, while the HCl condition does so indirectly (i.e. only as the cells produce it). Individual clones were selected after three rounds of subculturing and the plasmids carrying the mutant sigma factors were extracted. Fresh cells were retransformed by electroporation to make sure the improved phenotype did not arise due to spontaneous mutation of the chromosomal DNA. After the phenotype was confirmed, the best clones were selected for more detailed analysis; mutant S6 was isolated in the LA condition and mutant H13 in the HCl condition. FIG. 1 shows how these mutants perform compared to the control under the same stresses used for selecting them. Mutant S6 grows about 3.5-fold faster and to a 5-fold higher OD than the control in the LA condition. Mutant H13 reaches 86.4% higher OD and 25% higher growth rate than the control when grown in the HCl condition. The mutants were also tested in the condition not used for selection, i.e., mutant S6 was grown in the HCl condition and H13 in the LA condition. The results are summarized in Table 2.

TABLE 2

Growth rate (μ) and stationary phase optical density (600 nm) of the mutants and control under the experimental conditions.

| | LA condition | | HCl condition | |
|---|---|---|---|---|
| Strain | μ(hr$^{-1}$) | Stat. OD | μ(hr$^{-1}$) | Stat. OD |
| S6 | 0.101 ± 0.001 | 3.0 ± 0.1 | 0.08 ± 0.01 | 1.19 ± 0.01 |
| H13 | 0.057 ± 0.004 | 3.2 ± 0.2 | 0.151 ± 0.001 | 3.33 ± 0.08 |
| Wild-type | 0.028 ± 0.005 | 0.6 ± 0.2 | 0.12 ± 0.01 | 2.08 ± 0.02 |
| S6-H13 | 0.058 ± 0.004 | 2.9 ± 0.2 | 0.152 ± 0.002 | 3.02 ± 0.01 |

The mutant plasmids were sequenced in order to learn something about the mechanism behind the observed phenotypes. Surprisingly, mutant S6 carries a single nonsynonymous substitution that changed glutamine 345 to lysine. Mutant H13 carries several nonsynonymous substitutions (A44T, K74R, A114D, and A119S) and an insertion that results in a truncated sigma factor. The truncated polypeptide consists of the N-terminal 119 amino acids of the protein.

We also co-expressed the two rpoD mutants in the same cell as prior work suggested that improvements in phenotype conferred by different sigma factors may be additive (2). When tested in the LA, HCl, or non-stressful conditions, the growth and L-lactate production of the fused mutant was similar to that of H13 (Table 2, L-lactate data not shown).

Fermentations.

Figure 2:
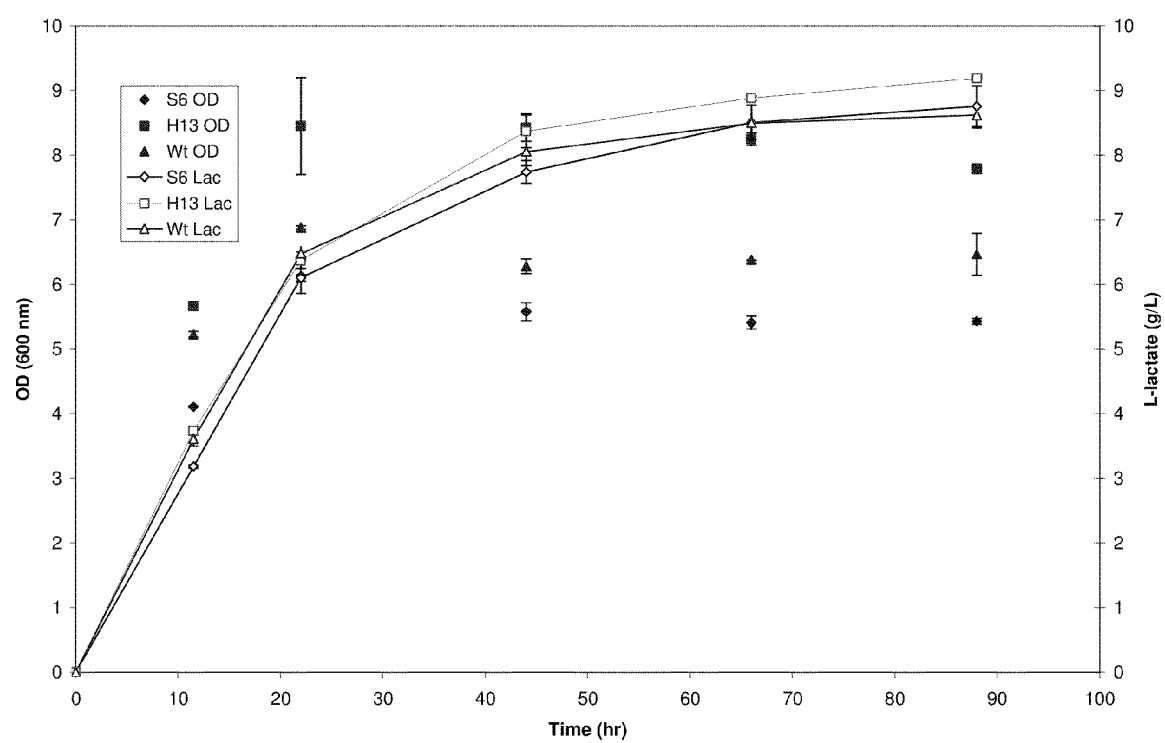
FIG. 2. Shake-flask fermentation of L-lactate by the mutants and control in media supplemented with glucose and unadjusted pH. Open symbols are for L-lactate (right axis) and closed symbols for $OD_{600}$ (left axis). Legend: Wt, wild-type; Lac, L-lactate; OD, optical density at 600 nm.
Figure 3:
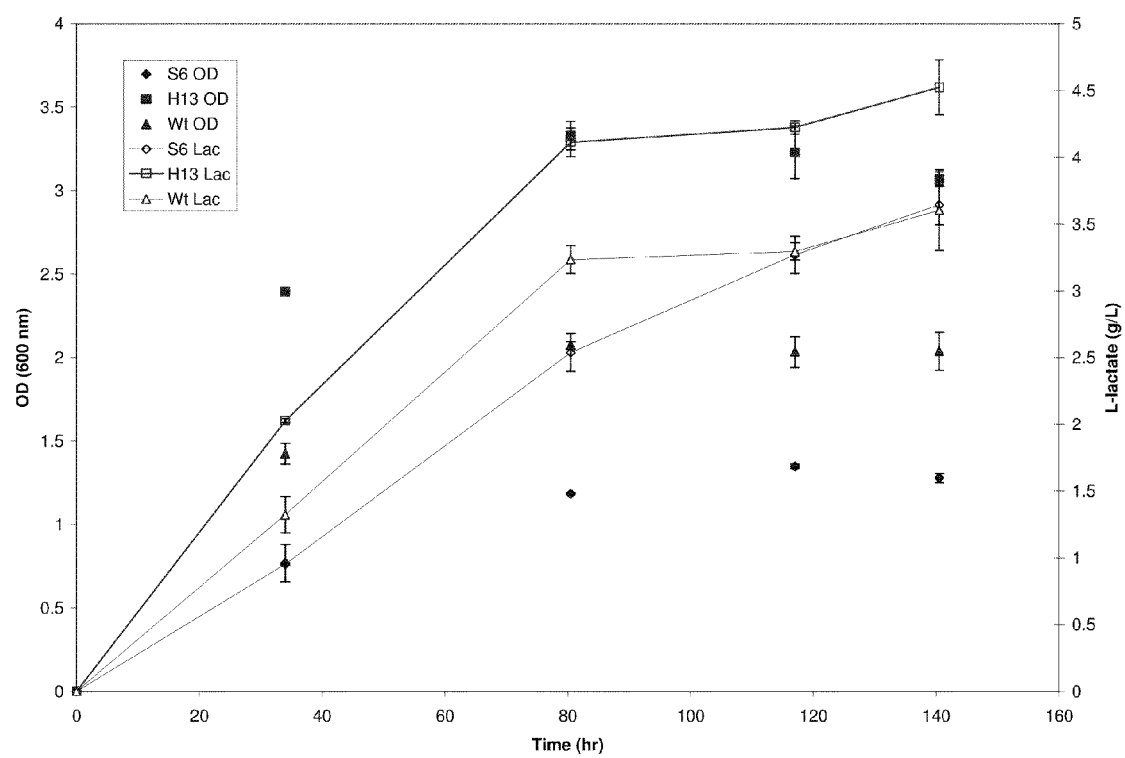
FIG. 3. Shake-flask fermentation of L-lactate in the HCl condition (initial pH=3.85±0.05). Legend and symbols as in FIG. 2.

Fermentations were done to determine the lactic acid productivity of mutants and control. Media was either supplemented to 100 g/L glucose (no stress) or the initial pH was adjusted to 3.85 with no added glucose (HCl condition). Under no stress, the two mutants and the control had similar lactic acid titers, except that strain S6 showed a slightly lower stationary OD resulting in a 20% increase in specific productivity (FIG. 2). At initial pH of 3.85, mutant H13 grew better and produced more lactic acid (FIG. 3). Mutant S6 reached L-lactate titers similar to those of the control, but again reached a lower OD. In this condition, the specific productivity was 60% larger.

Quantification of Phenotypic Diversity.

Combinatorial methods for surveying the phenotypic space, such as gTME, can be evaluated by the diversity they introduce in a population (i.e. a library). We chose colony size, related to growth rate, as the phenotype for quantifying diversity because it was easy to determine experimentally. The cells were plated in different conditions, the plates were photographed, and the colony sizes measured with image analysis software (MetaMorph 6.2).

Figure 4A:
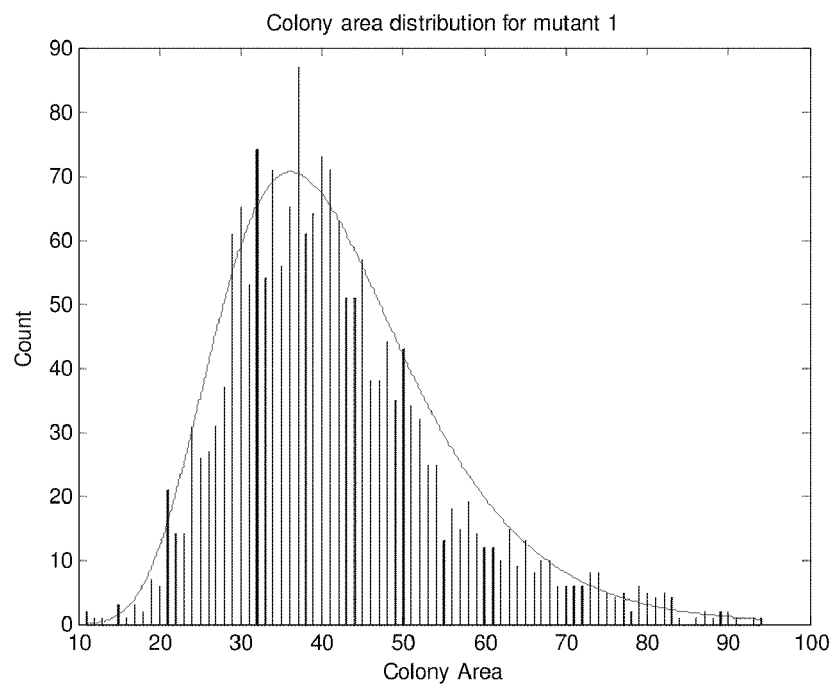
FIG. 4. (A,B) Distributions of colony sizes for each mutant plated separately. The smooth line was constructed by fitting the histogram to a lognormal distribution. (C) The graph shows the lines from A and B in the same plot for easier appreciation of the difference. (D) Silhouette analysis for a mixture of mutants 1 and 2. The silhouette value for each data point is a measure of how similar that point is to points in its own cluster compared to points in other clusters, and ranges from −1 to +1 (see Materials and Methods). The plot shows that the populations may be clearly separated in two clusters with members of large silhouette values (most are larger than 0.5).
Figure 4B:
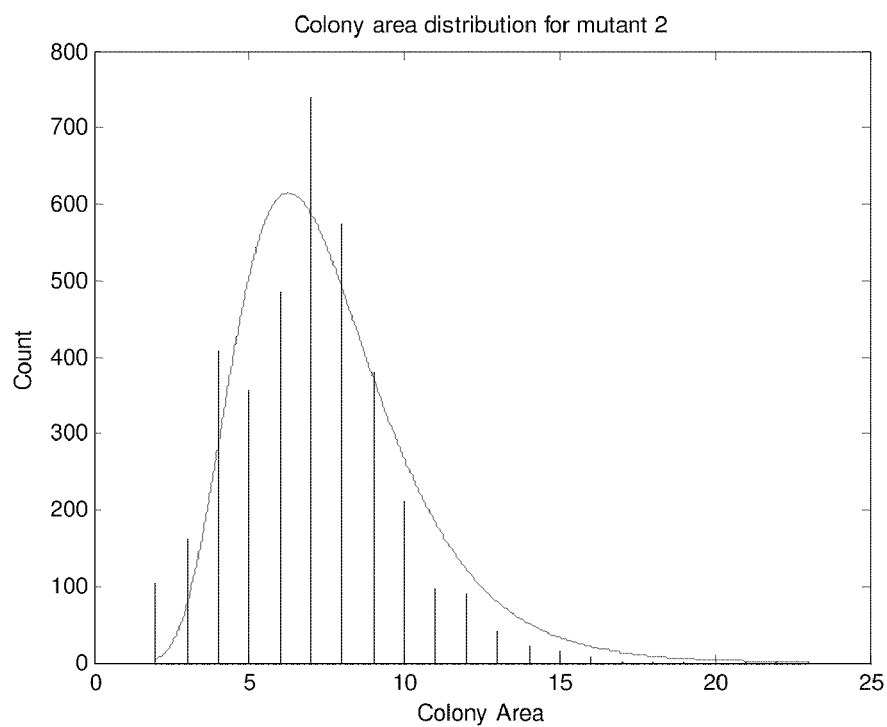
Figure 4C:
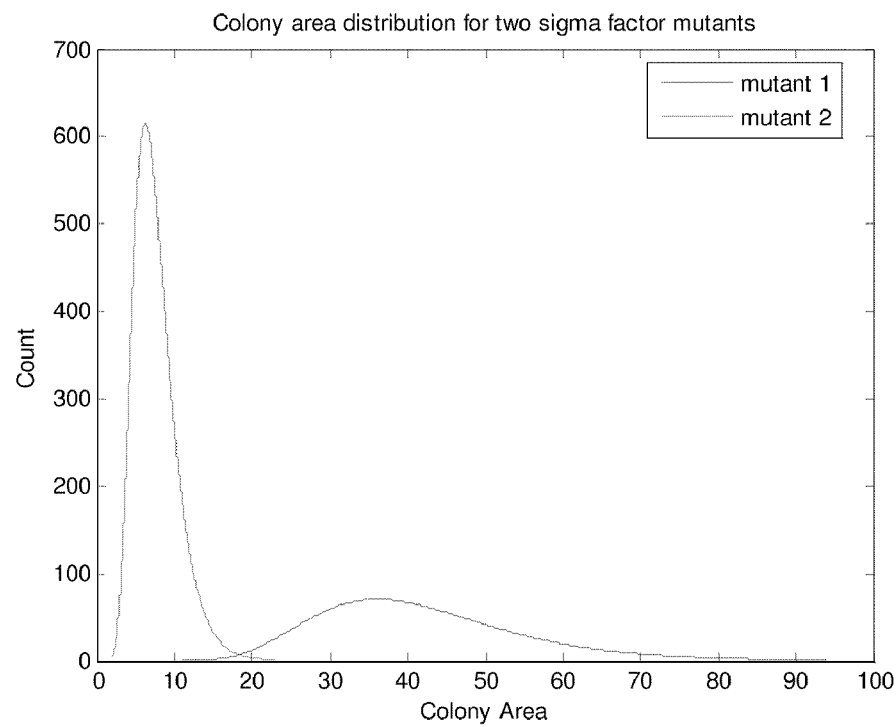
Figure 4D:
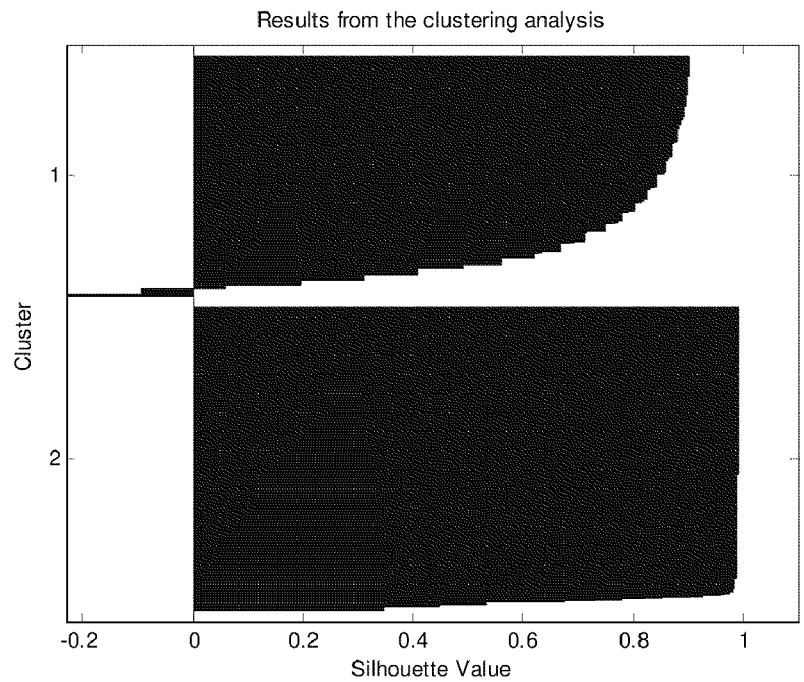

Before applying the method to the libraries, it was necessary to assess its efficacy for distinguishing colonies of various sizes. Two sigma factor mutants that formed colonies of different sizes were plated either separately or mixed (in a 50:50 mixture). First, the mutants plated independently were photographed and analyzed. As can be seen from FIGS. 4A and 4B, the sizes of clonal populations of both mutants follow the same distribution (roughly lognormal), but with very distinct values (FIG. 4C). The data produced by the mixed population was also analyzed to determine if a clustering algorithm could be used to separate the two clones based on colony size. FIG. 4D shows the silhouette value for the two clusters, a normalized measure of how similar is each individual to members of its own cluster compared to members of the other cluster; in general, this value ranges from −1 to +1 (see Materials and Methods). Most silhouette values in our analysis are close to +1, indicating that the clusters are tight and that this method can be used to distinguish mutants based on colony size.

Comparing the Phenotypic Diversity of Different Populations.

After the method itself was evaluated, it was used to quantify the phenotypic diversity of sigma factor libraries that differed in their average mutation frequencies. More than 4000 clones were plated in different conditions (low pH (adjusted with HCl), high osmotic pressure, high lactic acid, or non-stressful conditions) and their colony areas were analyzed.

Figure 5:
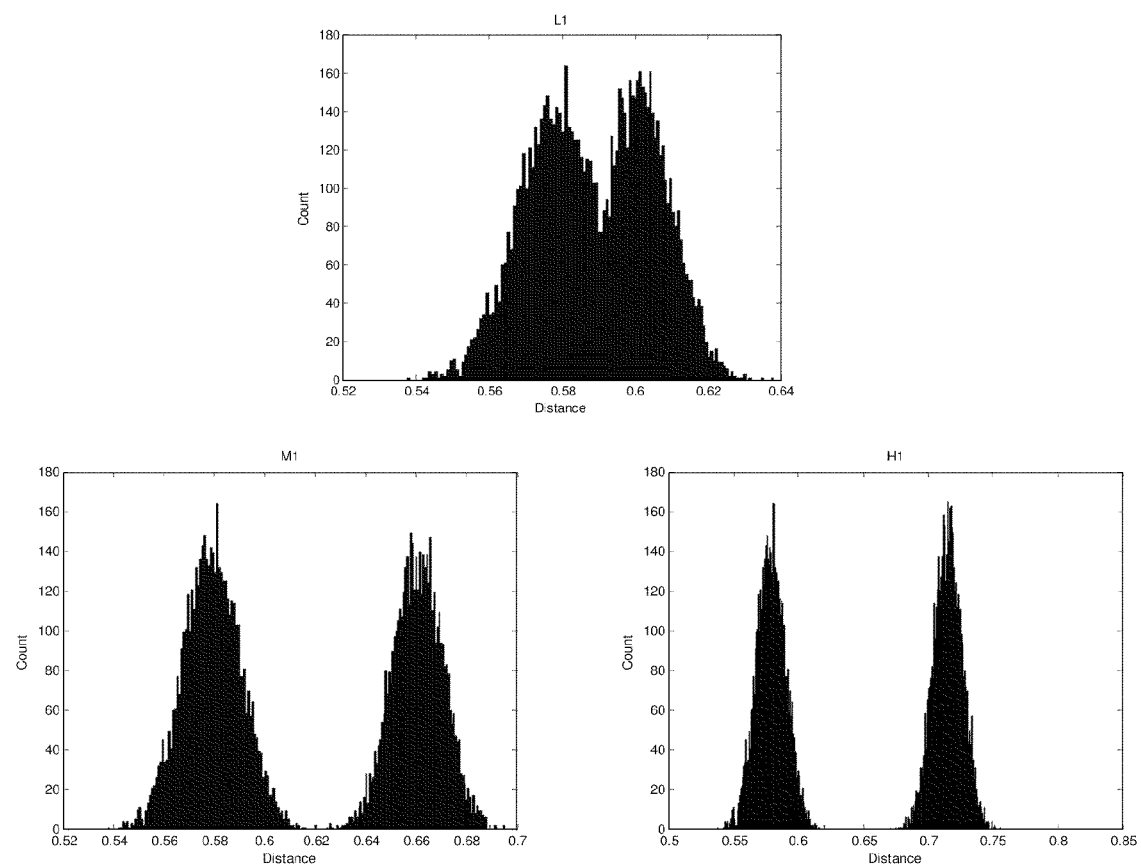
FIG. 5. Bootstrapped distances of the populations with different mutation frequencies under non-stressful conditions. The distance distribution of the unmutated control is included in the three plots (mean ~0.57) for comparison. L1, M1, and H1 refer to low, medium, and high mutation frequencies respectively. From the plots it is appreciable that M1 is farther to the control than L1, but closer than H1. For normalization, the distance of the control population was subtracted from the distance library population using Bhattacharyya's equation (see FIG. 6).

The average phenotypic distance was calculated for each population in the non-stressful condition. This value is a measure of how phenotypically dissimilar are members of a population, on average. The original size of each library ($>10^5$) is significantly larger than the number of clones that were analyzed, so the average phenotypic distance was bootstrapped to obtain its distribution (we assume that the sample is a good representation of the original population). FIG. 5 shows the results for the three mutation frequencies under non-stressful conditions as an example. In all three graphs the control is included for comparison (mean ~0.57). The graph shows that increasing the mutation frequency increases the average distance between the members of the populations. The analysis was repeated for each of the libraries (and control) plated in each of the other three conditions to see if this trend is also observed under stress. The result of the analysis is a 4×1 vector for each population whose entries are the average phenotypic distances in each of the conditions.

All populations, including those that are clonal, have a nonzero phenotypic distance, as there is inherent variability in their internal environments (11, 31). Therefore, the distance value by itself is meaningless unless it is properly normalized. The average phenotypic distance of a library population can be compared to that of the unmutated control, giving the "additional" distance introduced by the mutated sigma factors, here called "divergence". Because each entry of the distance vector is associated with a distribution of distance values (made by bootstrapping), this normalization must account for both the mean and the dispersion of the distributions. In general, this can be done using so-called statistical distance measures.

Figure 6:
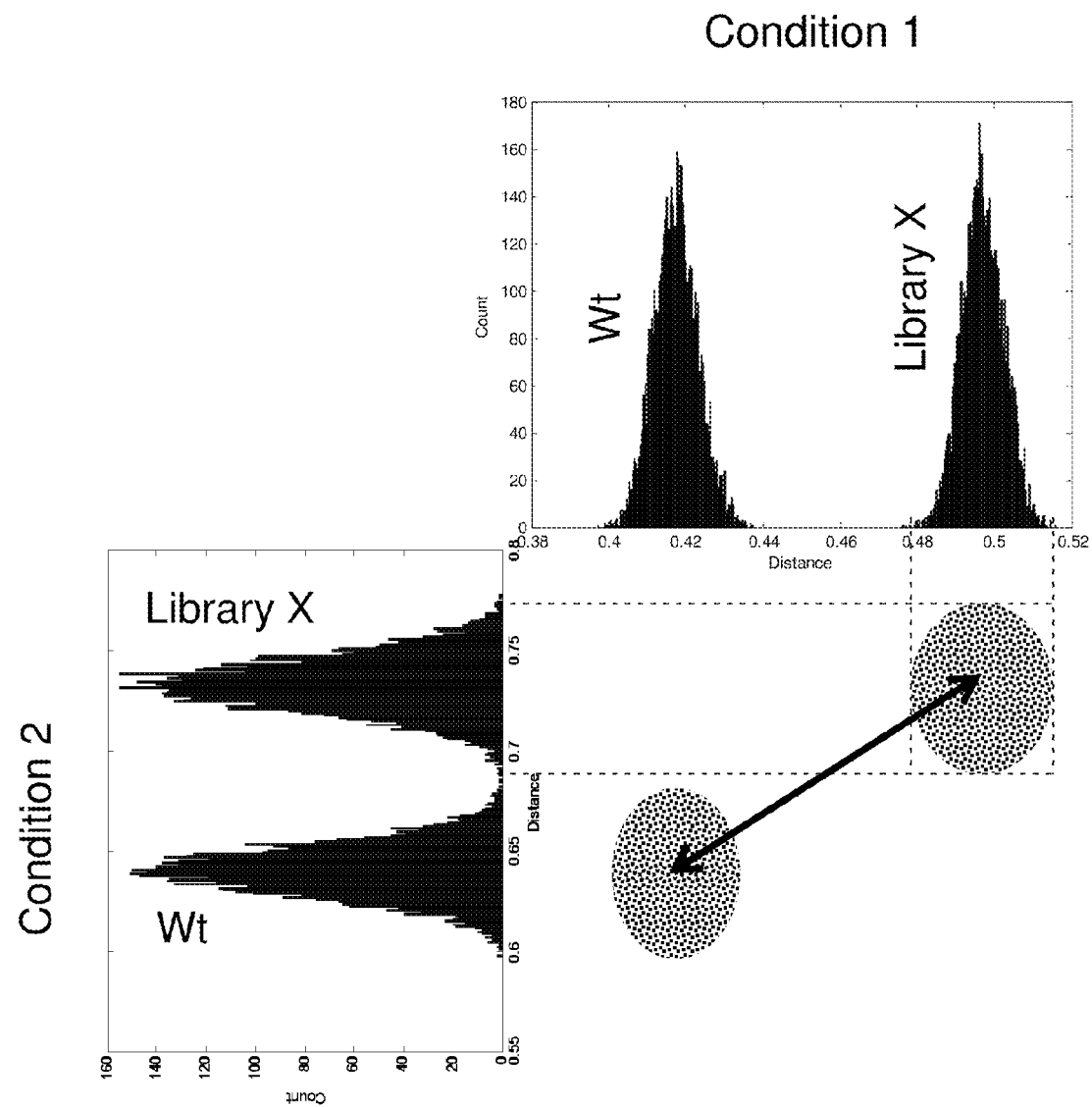
FIG. 6. Schematic illustration of the normalization method. The "divergence" is the average phenotypic distance of a library population compared to that of the control. In the diagram, the divergence is represented by the double-headed arrow, except that the statistical measure used (Bhattacharyya distance) accounts also for the dispersion of the distributions.

We chose the Bhattacharyya distance to normalize the vectors of each of the libraries by the vector of the control population. This is illustrated in FIG. 6 for the two-dimensional case. To visualize why is important to account for the dispersion, consider the case where the standard deviation of the two distributions in FIG. 6 increases while the mean is unchanged (i.e. the circles become larger but remain centered in the same place). As this happens, the difference between distributions diminishes, while the distance between the means does not. The Bhattacharyya distance between the library and control vectors is thus a statistically relevant measure of the divergence between these populations.

To add practical significance to this analysis, we carry out the same analysis for a population that has been mutagenized using NTG (N-Methyl-N'-nitro-N-nitrosoguanidine). This reagent is widely used to create diversity in a population for approaches such as classical strain improvement, in which serial rounds of mutagenesis and selection are used to isolate clones with valuable traits. The results of the analysis are summarized in FIG. 7.

Discussion

Recent studies in our laboratory indicate that mutagenesis of the principal sigma factor can be used to engineer complex phenotypes by altering the transcriptome globally (1, 2). We extended this concept to *Lactobacillus plantarum* for improving its growth in high lactic acid and low pH conditions. We constructed a sigma factor library and challenged it with high lactic acid (5.5 g/L of L-lactate at initial pH=4.6, LA condition) and at low pH (3.85, HCl condition). Mutants S6 and H13 were isolated in the above conditions respectively. We confirmed that the improved phenotype was caused by the mutant sigma factor by retransforming wild-type cells with the plasmid isolated from the screening. The retransformed mutant S6 reached a 5-fold higher OD in the LA condition, whereas mutant H13 a nearly 2-fold higher OD in the HCl condition.

Acidification of the media with inorganic acid causes a different transcriptomic response than when lactic acid is used (26), although these stresses are inseparable during fermentation. The production of lactic acid is accompanied by acidification of the media, while low pH increases the amount of free lactic acid that may enter the cell and effect toxicity (13, 19). Therefore, it is possible that the transcriptome that protects H13 at low pH (HCl condition) also protects it against lactic acid (LA condition). Conversely, the same may be true of S6 in the HCl condition. To explore this transcriptomic overlap, we tested the mutants and control in both conditions (Table 2). Mutant H13 exhibits improved growth at low pH adjusted with both inorganic and lactic acids, but mutant S6 does not when inorganic acid is used. Likely, the mutants cope with these stresses differently and the underlying mechanisms result in a convergent phenotype. We tried to exploit both mechanisms by co-expressing the mutant sigma factors in the same cell. The phenotype of the combined mutant in both LA and HCl was similar to that of H13, suggesting that the mechanism of action of this sigma factor is dominant over that of S6 and wild-type.

Fermentations were done to explore the lactic acid productivity of the mutants under no stress and at low pH. A mechanism that would reduce the production of lactic acid, the main cause of toxicity, could result in a strain with a higher apparent tolerance to lower pH. Furthermore, studies report that

*Lactobacillus plantarum* is capable of utilizing lactate (21), so it is possible that the mutants grow at the expense of the chemical we want to produce. Under no stress, all strains produced similar amounts of L-lactate, except that mutant S6 reached a slightly lower OD compared to the control. This results in a higher specific productivity of approximately 20%. At low pH, mutant H13 shows improved growth accompanied by an increase in lactic acid production. Mutant S6 again showed a lower OD but similar L-lactate titers that the wild-type, leading to a 60% higher specific productivity. The increase in specific productivity has been observed previously and is thought to be advantageous, as the cells divert resources to producing lactic acid instead of biomass (25).

We also studied the sequences of the mutant factors that gave rise to the observed characteristics. Mutant S6 has a single nonsynonymous substitution Q345K. This mutation was responsible for the increased growth in high lactic acid, the higher specific productivity of lactate, the intolerance to high salt (cells did not grow in 900 mM NaCl), and probably other traits that remain uncharacterized. The pleiotropic nature of the mutation suggests that it changes the internal environment globally. Glutamine 345 is located in a region that is highly conserved across sigma factors of many species, and is involved in the recognition of and interaction with the −35 promoter box (7). This mutation most likely changes the relative affinity of the RNA polymerase (RNAP) holoenzyme for different promoter regions resulting in a global response.

Mutant H13 has several nonsynonymous substitutions and an insertion that results in a truncated sigma factor that includes all of region 1.1 and part of region 1.2 of the protein. Region 1.1 is relatively unconserved across species. Many bacterial sigma factors (like that of *E. coli*) have acidic N-terminals, presumably to mimic the DNA strand and prevent nonspecific binding of the sigma subunit when not bound to the core RNAP (9). Others (like that of *Thermosynechococcus elongates*) have basic regions that have been suggested to be involved in direct DNA binding (15). We analyzed the first 70 amino acids of mutant H13, and found 12 basic residues, contrasting with 3 in the *E. coli* counterpart. This suggests that it is possible that region 1.1 of the *Lactobacillus* sigma subunit binds DNA and that the free form acts as a nonspecific repressor. The 3-D structure of the *Lactobacillus* sigma subunit has not been determined, which precluded us from doing a surface charge analysis to assess this possibility. A more complete explanation of the effect of mutant H13 on the transcription process would require a multifaceted study and thus is beyond the scope of the present example.

The results hitherto discussed, along with previous studies in *S. cerevisiae* and *E. coli*, establish the practical usefulness of the gTME approach, but its efficacy has not been linked to a fundamental property of the studied libraries. In the present study we tried to place this issue in a framework that can be extended to other strain improvement methods. We reasoned that diversity is an intrinsic property of a population and that it can be used as a proxy of its evolutionary potential. We used growth rate under different conditions as the phenotype for diversity quantification; using image analysis software, the area of colonies bearing different sigma factors was measured. After testing the method for distinguishing two mutants based on colony size, it was used to quantify the divergence of sigma factor and NTG-mutagenesis libraries from an unmutated control. Nitrosoguanidine (NTG) is a chemical frequently used for mutagenesis in classical strain improvement that effects random widespread mutations throughout the genome.

The results of the analysis support the following conclusions: (i) that mutations in the sigma factor allow introduction of phenotypic diversity; (ii) that this variability increases with mutation frequency; (iii) that localized mutagenesis of the sigma factor enhances diversity better than NTG mutagenesis of the entire genome; and (iv) that the increased diversity is observed in different conditions (i.e. the mutations are pleiotropic).

Figure 7:
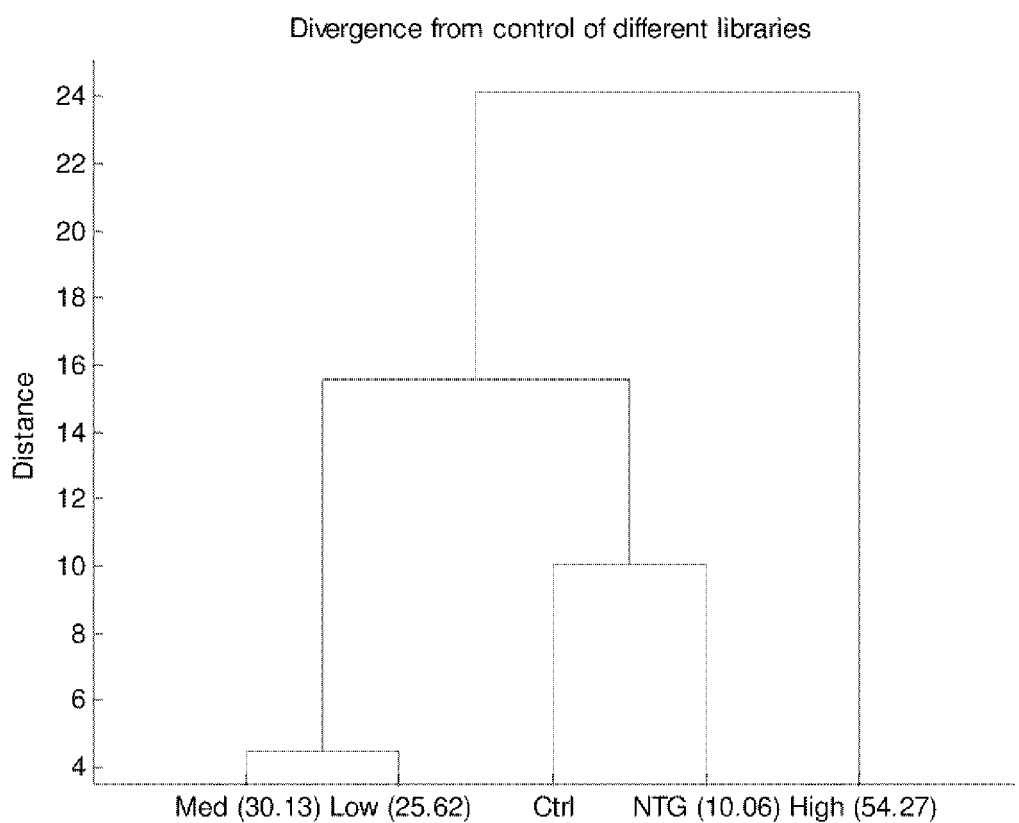
FIG. 7. The dendrogram was constructed with the normalized distance of each library (i.e. the control value is zero by definition). The Bhattacharyya distance (divergence) value is in parenthesis next to the name of the library. The diagram shows that the NTG library is closest in diversity to the control, while the sigma factor library with high mutation frequency is farthest.

Conclusion (ii) should not be considered a general trend, as it is expected that at a high enough mutation frequency most of the resulting sigma factors would be nonfunctional. In such a library, the variability in phenotype should be closer to that of the wild-type (the experimental setup only allows observation of dominant phenotypes). Populations of the medium and low mutation frequencies are closer in diversity than those of medium and high frequencies, as shown in FIG. 7. This makes sense in light of the experimental procedure used to obtain the libraries: the "medium" mutation frequency library was prepared with half the template than that of the "low", while the "high" was prepared with one tenth of that in the "medium". Therefore, the terms low, medium, and high, do not reflect a "linear" increase in mutation frequencies. Conclusions (iii) and (iv) have important practical consequences; the former because it establishes that targeting the global transcription machinery is fundamentally useful in evolving new strains, the latter because it evidences the versatility of this approach.

The fact that mutagenesis at the chromosomal level was less effective than localized mutagenesis of the sigma factor may seem counterintuitive. After all, it may be argued, mutations in the sigma factor are a subset of the possible mutations in the chromosome. However, because the mutations are introduced in an additional copy of the sigma factor, we are effectively evolving an "alternative" sigma factor that confers the improved response. This mimics the process of gene duplication and function specialization that may have lead to naturally occurring alternative sigma factors (12).

The present and similar approaches recognize that the stress responses are more closely linked to the transcriptome than to the genotype. The fact that we have successfully extended this technique to several species suggests that this principle is universal. The concept is not limited to the sigma factor and current efforts in our group are trying to identify other regulators for manipulating the transcriptome and proteome globally. We present a diversity quantification method that will help assess the potential of these targets. Also, this method can guide targeting mutations to different regions of the sigma factor or of other proteins so that the sequence space is explored more efficiently.

REFERENCES

1. Alper, H., J. Moxley, E. Nevoigt, G. R. Fink, and G. Stephanopoulos. 2006. Engineering yeast transcription machinery for improved ethanol tolerance and production. Science 314:1565-8.
2. Alper, H., and G. Stephanopoulos. 2007. Global transcription machinery engineering: A new approach for improving cellular phenotype. Metab Eng 9:258-67.
3. Aukrust, T. W., M. B. Brurberg, and I. F. Nes. 1995. Transformation of *Lactobacillus* by electroporation. Methods Mol Biol 47:201-8.
4. Azcarate-Peril, M. A., E. Altermann, R. L. Hoover-Fitzula, R. J. Cano, and T. R. Klaenhammer. 2004. Identification and inactivation of genetic loci involved with *Lactobacillus acidophilus* acid tolerance. Appl Environ Microbiol 70:5315-22.
5. Beltran, A., Y. Liu, S. Parikh, B. Temple, and P. Blancafort. 2006. Interrogating genomes with combinatorial artificial transcription factor libraries: asking zinc finger questions. Assay Drug Dev Technol 4:317-31.
6. Booth, I. R. 1985. Regulation of cytoplasmic pH in bacteria. Microbiol Rev 49:359-78.
7. Campbell, E. A., O. Muzzin, M. Chlenov, J. L. Sun, C. A. Olson, O. Weinman, M. L. Trester-Zedlitz, and S. A. Darst. 2002. Structure of the bacterial RNA polymerase promoter specificity sigma subunit. Mol Cell 9:527-39.
8. Day, D. A., and M. F. Tuite. 1998. Post-transcriptional gene regulatory mechanisms in eukaryotes: an overview. J Endocrinol 157:361-71.
9. Dombroski, A. J., W. A. Walter, M. T. Record, Jr., D. A. Siegele, and C. A. Gross. 1992. Polypeptides containing highly conserved regions of transcription initiation factor sigma 70 exhibit specificity of binding to promoter DNA. Cell 70:501-12.
10. Duy, N. V., U. Mader, N. P. Tran, J. F. Cavin, T. Tam le, D. Albrecht, M. Hecker, and H. Antelmann. 2007. The proteome and transcriptome analysis of Bacillus subtilis in response to salicylic acid. Proteomics 7:698-710.
11. Elowitz, M. B., A. J. Levine, E. D. Siggia, and P. S. Swain. 2002. Stochastic gene expression in a single cell. Science 297:1183-6.
12. Errington, J. 1991. Possible intermediate steps in the evolution of a prokaryotic developmental system. Proc Biol Sci 244:117-21.
13. Giraud, E., B. Lelong, and M. Raimbault. 1991. Influence of Ph and Initial Lactate Concentration on the Growth of Lactobacillus-Plantarum. Applied Microbiology and Biotechnology 36:96-99.
14. Hansen, M. E., F. Lund, and J. M. Carstensen. 2003. Visual clone identification of Penicillium commune isolates. J Microbiol Methods 52:221-9.
15. Imashimizu, M., M. Hanaoka, A. Seki, K. S. Murakami, and K. Tanaka. 2006. The cyanobacterial principal sigma factor region 1.1 is involved in DNA-binding in the free form and in transcription activity as holoenzyme. FEBS Lett 580:3439-44.
16. Kleerebezem, M., J. Boekhorst, R. van Kranenburg, D. Molenaar, O. P. Kuipers, R. Leer, R. Tarchini, S. A. Peters, H. M. Sandbrink, M. W. Fiers, W. Stiekema, R. M. Lankhorst, P. A. Bron, S. M. Hoffer, M. N. Groot, R. Kerkhoven, M. de Vries, B. Ursing, W. M. de Vos, and R. J. Siezen. 2003. Complete genome sequence of Lactobacillus plantarum WCFS1. Proc Natl Acad Sci USA 100: 1990-5.
17. Kok, J., J. M. van der Vossen, and G. Venema. 1984. Construction of plasmid cloning vectors for lactic streptococci which also replicate in Bacillus subtilis and Escherichia coli. Appl Environ Microbiol 48:726-31.
18. Kresnowati, M. T., C. Suarez-Mendez, M. K. Groothuizen, W. A. van Winden, and J. J. Heijnen. 2007. Measurement of fast dynamic intracellular pH in Saccharomyces cerevisiae using benzoic acid pulse. Biotechnol Bioeng 97:86-98.
19. McDonald, L. C., H. P. Fleming, and H. M. Hassan. 1990. Acid Tolerance of Leuconostoc mesenteroides and Lactobacillus plantarum. Appl Environ Microbiol 56:2120-2124.
20. Miller, J. H. 1972. Experiments in molecular genetics, p. 125-129. Cold Spring Harbor Laboratory, Cold Spring Harbor, N.Y.
21. Murphy, M. G., L. O'Connor, D. Walsh, and S. Condon. 1985. Oxygen dependent lactate utilization by Lactobacillus plantarum. Arch Microbiol 141:75-9.
22. Park, K. S., Y. S. Jang, H. Lee, and J. S. Kim. 2005. Phenotypic alteration and target gene identification using combinatorial libraries of zinc finger proteins in prokaryotic cells. J Bacteriol 187:5496-9.
23. Park, K. S., D. K. Lee, H. Lee, Y. Lee, Y. S. Jang, Y. H. Kim, H. Y. Yang, S. I. Lee, W. Seol, and J. S. Kim. 2003. Phenotypic alteration of eukaryotic cells using randomized libraries of artificial transcription factors. Nat Biotechnol 21:1208-14.
24. Park, K. S., W. Seol, H. Y. Yang, S. I. Lee, S. K. Kim, R. J. Kwon, E. J. Kim, Y. H. Roh, B. L. Seong, and J. S. Kim. 2005. Identification and use of zinc finger transcription factors that increase production of recombinant proteins in yeast and mammalian cells. Biotechnol Prog 21:664-70.
25. Patnaik, R., S. Louie, V. Gavrilovic, K. Perry, W. P. Stemmer, C. M. Ryan, and S. del Cardayre. 2002. Genome shuffling of Lactobacillus for improved acid tolerance. Nat Biotechnol 20:707-12.
26. Pieterse, B., R. J. Leer, F. H. Schuren, and M. J. van der Werf. 2005. Unravelling the multiple effects of lactic acid stress on Lactobacillus plantarum by transcription profiling. Microbiology 151:3881-94.
27. Porro, D., M. M. Bianchi, L. Brambilla, R. Menghini, D. Bolzani, V. Carrera, J. Lievense, C. L. Liu, B. M. Ranzi, L. Frontali, and L. Alberghina. 1999. Replacement of a metabolic pathway for large-scale production of lactic acid from engineered yeasts. Appl Environ Microbiol 65:4211-5.
28. Posno, M., R. J. Leer, N. van Luijk, M. J. van Giezen, P. T. Heuvelmans, B. C. Lokman, and P. H. Pouwels. 1991. Incompatibility of Lactobacillus Vectors with Replicons Derived from Small Cryptic Lactobacillus Plasmids and Segregational Instability of the Introduced Vectors. Appl Environ Microbiol 57:1822-1828.
29. Stephanopoulos, G. 2002. Metabolic engineering by genome shuffling. Nat Biotechnol 20:666-8.
30. Stephanopoulos, G., H. Alper, and J. Moxley. 2004. Exploiting biological complexity for strain improvement through systems biology. Nat Biotechnol 22:1261-7.
31. Swain, P. S., M. B. Elowitz, and E. D. Siggia. 2002. Intrinsic and extrinsic contributions to stochasticity in gene expression. Proc Natl Acad Sci USA 99:12795-800.
32. Zhang, Y. X., K. Perry, V. A. Vinci, K. Powell, W. P. Stemmer, and S. B. del Cardayre. 2002. Genome shuffling leads to rapid phenotypic improvement in bacteria. Nature 415:644-6.
33. Kresnowati M T A P, et al. 2007. Measurement of fast dynamic intracellular pH in Saccharomyces cerevisiae, using benzoic acid pulse. Biotechnology and Bioengineering 97: 86-98.
34. Franck P, et al. 1996. Measurement of intracellular pH in cultured cells by flow cytometry with BCECF-AM. J Biotechnol 46: 187-95.
35. Spilimbergo S, Bertucco A, Basso G, Bertoloni G. 2005. Determination of extracellular and intracellular pH of Bacillus subtilis suspension under CO2 treatment. Biotechnol Bioeng 92: 447-51.

Those skilled in the art will recognize, or be able to ascertain using no more than routine experimentation, many equivalents to the specific embodiments of the invention described herein. Such equivalents are intended to be encompassed by the following claims.

All references disclosed herein are incorporated by reference in their entirety for the purposes disclosed above.

We claim:

1. A mutant sigma factor comprising a nonsynonymous substitution of glutamine 345 (Q345) in *Lactobacillus plantarum* RpoD (SEQ ID NO:11), or the equivalent amino acid in other sigma factors of *Lactobacillus* or of other bacterial strains, wherein the sigma factor does not comprise a truncation.

2. The mutant sigma factor of claim 1, wherein the sigma factor is rpoD, rpoF, rpoS, rpoH, rpoN, rpoE, fed or sigH.

3. The sigma factor of claim 2, wherein the sigma factor is rpoD.

4. The sigma factor of claim 1, wherein the bacterial strain is an *E. coli* strain.

5. The mutant *Lactobacillus* sigma factor of claim 1, wherein the nonsynonymous substitution is a lysine (Q345K) in rpoD.

* * * * *

UNITED STATES PATENT AND TRADEMARK OFFICE
CERTIFICATE OF CORRECTION

| | | |
|---|---|---|
| PATENT NO. | : 8,193,314 B2 | |
| APPLICATION NO. | : 12/170617 | |
| DATED | : June 5, 2012 | |
| INVENTOR(S) | : Gregory Stephanopoulos | |

It is certified that error appears in the above-identified patent and that said Letters Patent is hereby corrected as shown below:

Please delete the paragraph titled 'GOVERNMENT INTEREST' encompassing column 1, line 12-14:

"This work was funded in part by the National Science Foundation under grant number 6895619. The government has certain rights in this invention."

and replace with:

--This invention was made with government support under Grant No. BES0331364 awarded by the National Science Foundation. The government has certain rights in this invention.--

Signed and Sealed this
Twenty-seventh Day of November, 2012

David J. Kappos
*Director of the United States Patent and Trademark Office*

UNITED STATES PATENT AND TRADEMARK OFFICE
CERTIFICATE OF CORRECTION

PATENT NO. : 8,193,314 B2  
APPLICATION NO. : 12/170617  
DATED : June 5, 2012  
INVENTOR(S) : Gregory Stephanopoulos et al.

Page 1 of 1

It is certified that error appears in the above-identified patent and that said Letters Patent is hereby corrected as shown below:

In the claims:

At column 31, claim number 2, line 47, "fed" should be replaced to read --fecl--

Signed and Sealed this
Twelfth Day of July, 2016

Michelle K. Lee
*Director of the United States Patent and Trademark Office*

SEQUENCE LISTING

<160> NUMBER OF SEQ ID NOS: 11

<210> SEQ ID NO 1
<211> LENGTH: 35
<212> TYPE: DNA
<213> ORGANISM: Artificial Sequence
<220> FEATURE:
<223> OTHER INFORMATION: Oligonucleotide

<400> SEQUENCE: 1
gcgcgcatcg attgagtgag ctgataccgc tcgcc        35

<210> SEQ ID NO 2
<211> LENGTH: 28
<212> TYPE: DNA
<213> ORGANISM: Artificial Sequence
<220> FEATURE:
<223> OTHER INFORMATION: Oligonucleotide

<400> SEQUENCE: 2
gcgcatgcat cgtcagcggg tgttggcg        28

<210> SEQ ID NO 3
<211> LENGTH: 34
<212> TYPE: DNA
<213> ORGANISM: Artificial Sequence
<220> FEATURE:
<223> OTHER INFORMATION: Oligonucleotide

<400> SEQUENCE: 3
gcgccccggg tttggttcag cagttaacgt tggc        34

<210> SEQ ID NO 4
<211> LENGTH: 88
<212> TYPE: DNA
<213> ORGANISM: Artificial Sequence
<220> FEATURE:
<223> OTHER INFORMATION: Oligonucleotide

<400> SEQUENCE: 4
gcgctctaga aaatagccc aaaacctcgt taggagattt tgggctattt tatcgatggt        60
tagtcagacg tcatcatctg gtgattat        88

<210> SEQ ID NO 5
<211> LENGTH: 32
<212> TYPE: DNA
<213> ORGANISM: Artificial Sequence
<220> FEATURE:
<223> OTHER INFORMATION: Oligonucleotide

<400> SEQUENCE: 5
ggcgcgcctt tggttcagca gttaacgttg gc        32

<210> SEQ ID NO 6
<211> LENGTH: 22
<212> TYPE: DNA
<213> ORGANISM: Artificial Sequence
<220> FEATURE:
<223> OTHER INFORMATION: Oligonucleotide

<400> SEQUENCE: 6
taaaacgacg gccagtgcca ag        22

<210> SEQ ID NO 7

```
<211> LENGTH: 37
<212> TYPE: DNA
<213> ORGANISM: Artificial Sequence
<220> FEATURE:
<223> OTHER INFORMATION: Oligonucleotide

<400> SEQUENCE: 7
ggcgcgccaa aatagcccaa aacctcgtta ggagatt                              37

<210> SEQ ID NO 8
<211> LENGTH: 30
<212> TYPE: DNA
<213> ORGANISM: Artificial Sequence
<220> FEATURE:
<223> OTHER INFORMATION: Oligonucleotide

<400> SEQUENCE: 8
aggaaacagc tatgacatga ttacgaattc                                     30

<210> SEQ ID NO 9
<211> LENGTH: 36
<212> TYPE: DNA
<213> ORGANISM: Artificial Sequence
<220> FEATURE:
<223> OTHER INFORMATION: Oligonucleotide

<400> SEQUENCE: 9 tacttttttac agtcggtttt ctaatgtcac taacct                             36

<210> SEQ ID NO 10
<211> LENGTH: 36
<212> TYPE: DNA
<213> ORGANISM: Artificial Sequence
<220> FEATURE:
<223> OTHER INFORMATION: Oligonucleotide

<400> SEQUENCE: 10
aattgacgat ttaaacaata ttagctttga acaatt                              36

<210> SEQ ID NO 11
<211> LENGTH: 368
<212> TYPE: PRT
<213> ORGANISM: Lactobacillus plantarum

<400> SEQUENCE: 11
```

| Met | Ala | Lys | Ala | Lys | Ala | Thr | Thr | Glu | Tyr | Asp | Lys | Ala | Val | Lys | Ala |
|---|---|---|---|---|---|---|---|---|---|---|---|---|---|---|---|
| 1 | | | | 5 | | | | | 10 | | | | | 15 | |

| Leu | Ile | Lys | Glu | Tyr | Lys | Lys | Thr | Gly | Ser | Ile | Gln | Tyr | Asp | Glu | Leu |
|---|---|---|---|---|---|---|---|---|---|---|---|---|---|---|---|
| | | 20 | | | | | 25 | | | | | 30 | | | |

| Ser | Asp | Lys | Leu | Ala | Ala | Pro | Tyr | Lys | Leu | Asp | Ala | Ser | Gly | Ile | Asp |
|---|---|---|---|---|---|---|---|---|---|---|---|---|---|---|---|
| | | | 35 | | | | | 40 | | | | | 45 | | |

| Lys | Leu | Leu | Gln | Lys | Val | Glu | Asp | Ala | Gly | Ile | Ser | Val | Val | Asp | Glu |
|---|---|---|---|---|---|---|---|---|---|---|---|---|---|---|---|
| | 50 | | | | | 55 | | | | | 60 | | | | |

| Lys | Gly | Asp | Pro | Asp | Ala | Arg | Ala | Val | Lys | Ser | Val | Lys | Val | Ser |
|---|---|---|---|---|---|---|---|---|---|---|---|---|---|---|
| 65 | | | | 70 | | | | | 75 | | | | | 80 |

| Lys | Lys | Glu | Leu | Ser | Asp | Ala | Gly | Ser | Ala | Ser | Gly | Ile | Lys | Ile | Asn |
|---|---|---|---|---|---|---|---|---|---|---|---|---|---|---|---|
| | | | | 85 | | | | | 90 | | | | | 95 | |

| Asp | Pro | Val | Arg | Met | Tyr | Leu | Lys | Glu | Ile | Gly | Arg | Val | Asp | Leu | Leu |
|---|---|---|---|---|---|---|---|---|---|---|---|---|---|---|---|
| | | | 100 | | | | | 105 | | | | | 110 | | |

| Thr | Ala | Asp | Glu | Glu | Val | Ala | Leu | Ala | Leu | Arg | Ile | Glu | Gln | Gly | Asp |
|---|---|---|---|---|---|---|---|---|---|---|---|---|---|---|---|
| | | 115 | | | | | 120 | | | | | 125 | | | |

| Glu | Ser | Ala | Lys | Gln | Glu | Leu | Ala | Glu | Ala | Asn | Leu | Arg | Leu | Val | Val |
|---|---|---|---|---|---|---|---|---|---|---|---|---|---|---|---|
| | 130 | | | | | 135 | | | | | 140 | | | | |

-continued

```
Ser Ile Ala Lys Arg Tyr Val Gly Arg Gly Met Gln Phe Leu Asp Leu
145             150                 155                 160

Ile Gln Glu Gly Asn Met Gly Leu Met Lys Ala Val Glu Lys Phe Asp
                165                 170                 175

Tyr Arg Lys Gly Phe Lys Phe Ser Thr Tyr Ala Thr Trp Trp Ile Arg
            180             185                 190

Gln Ala Ile Thr Arg Ala Ile Ala Asp Gln Ala Arg Thr Ile Arg Ile
        195                 200                 205

Pro Val His Met Val Glu Thr Ile Asn Lys Leu Ile Arg Ile Gln Arg
        210                 215                 220

Gln Leu Leu Gln Asp Leu Gly Arg Glu Pro Thr Pro Glu Glu Ile Gly
225             230                 235                 240

Ala Glu Met Asp Met Pro Thr Glu Lys Val Arg Glu Ile Leu Lys Ile
                245                 250                 255

Ala Gln Glu Pro Val Ser Leu Glu Thr Pro Ile Gly Glu Glu Asp Asp
                260                 265                 270

Ser His Leu Gly Asp Phe Ile Glu Asp Gln Asp Ala Thr Ser Pro Ala
            275                 280                 285

Asp Ala Ala Tyr Glu Leu Leu Lys Glu Gln Leu Glu Gly Val Leu
            290             295                 300

Asp Thr Leu Thr Asp Arg Glu Glu Asn Val Leu Arg Leu Arg Phe Gly
305             310                 315                 320

Leu Asp Asp Gly Arg Thr Arg Thr Leu Glu Glu Val Gly Lys Val Phe
                325             330                 335

Gly Val Thr Arg Glu Arg Ile Arg Gln Ile Glu Ala Lys Ala Leu Arg
            340                 345                 350

Lys Leu Arg His Pro Ser Arg Ser Lys Gln Leu Lys Asp Phe Leu Glu
            355                 360                 365
```